United States Patent
Arndt et al.

[11] Patent Number: 5,904,709
[45] Date of Patent: May 18, 1999

[54] MICROWAVE TREATMENT FOR CARDIAC ARRHYTHMIAS

[75] Inventors: G. Dickey Arndt, Friendswood; James R. Carl, Houston; George W. Raffoul, Houston; Antonio Pacifico, Houston, all of Tex.

[73] Assignee: The United States of America as represented by the Administrator of the National Aeronautics and Space Administration, Washington, D.C.

[21] Appl. No.: 08/641,045

[22] Filed: Apr. 17, 1996

[51] Int. Cl.⁶ .......................................................... A61F 2/00
[52] U.S. Cl. .......................... 607/101; 607/156; 607/122; 606/33; 606/42
[58] Field of Search ...................................... 607/154–156, 607/100–102, 115–116, 122–123; 606/33–35, 37–40, 41–42, 45–50; 604/22

[56] References Cited

U.S. PATENT DOCUMENTS

| | | | |
|---|---|---|---|
| 4,641,649 | 2/1987 | Walinsky et al. | 607/122 X |
| 5,057,106 | 10/1991 | Kasevich et al. | 606/33 X |
| 5,370,644 | 12/1994 | Langberg | 606/33 X |
| 5,405,346 | 4/1995 | Grundy et al. | 607/101 X |
| 5,683,382 | 11/1997 | Lenihan et al. | 607/156 X |

*Primary Examiner*—Jeffrey R. Jastrzab
*Assistant Examiner*—Ryan Carter
*Attorney, Agent, or Firm*—Hardie R. Barr

[57] ABSTRACT

Method and apparatus are provided for propagating microwave energy into heart tissues to produce a desired temperature profile therein at tissue depths sufficient for thermally ablating arrhythmogenic cardiac tissue to treat ventricular tachycardia and other arrhythmias while preventing excessive heating of surrounding tissues, organs, and blood. A wide bandwidth double-disk antenna (700) is effective for this purpose over a bandwidth of about six gigahertz. A computer simulation provides initial screening capabilities for an antenna such as antenna, frequency, power level, and power application duration. The simulation also allows optimization of techniques for specific patients or conditions. In operation, microwave energy between about 1 Gigahertz and 12 Gigahertz is applied to monopole microwave radiator (600) having a surface wave limiter (606). A test setup provides physical testing of microwave radiators (854) to determine the temperature profile created in actual heart tissue or ersatz heart tissue (841). Saline solution (872) pumped over the heart tissue (841) with a peristaltic pump (862) simulates blood flow. Optical temperature sensors (838) disposed at various tissue depths within the heart tissue (841) detect the temperature profile without creating any electromagnetic interference. The method may be used to produce a desired temperature profile in other body tissues reachable by catheter (510) such as tumors and the like.

15 Claims, 8 Drawing Sheets

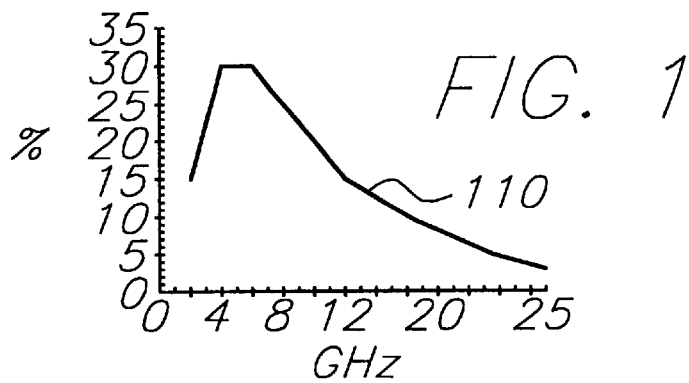
FIG. 1
| F(GHz) | VOL(MM³) | ΔT(°C) |
|--------|----------|--------|
| 2.45 | 7583 | 53 |
| 4.45 | 5700 | 72 |
| 6.45 | 4623 | 75 |
FIG. 2
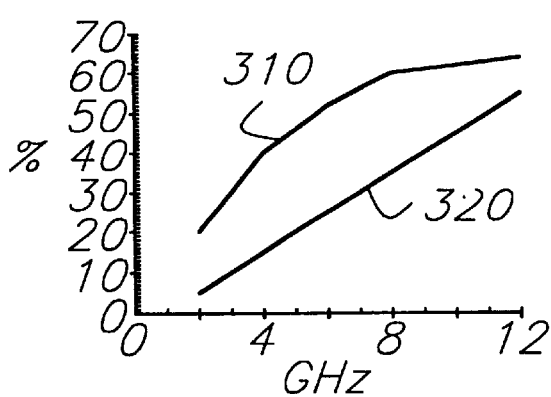
FIG. 3
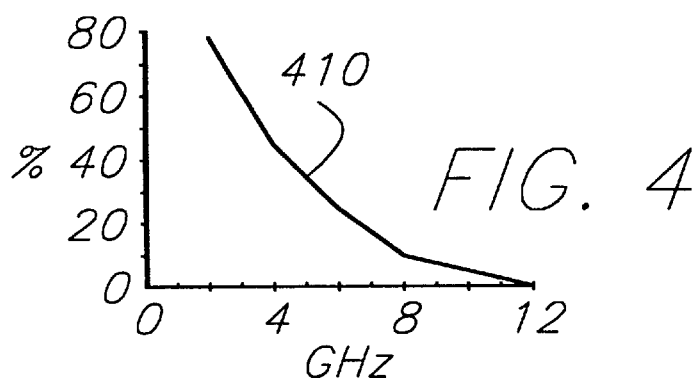
FIG. 4

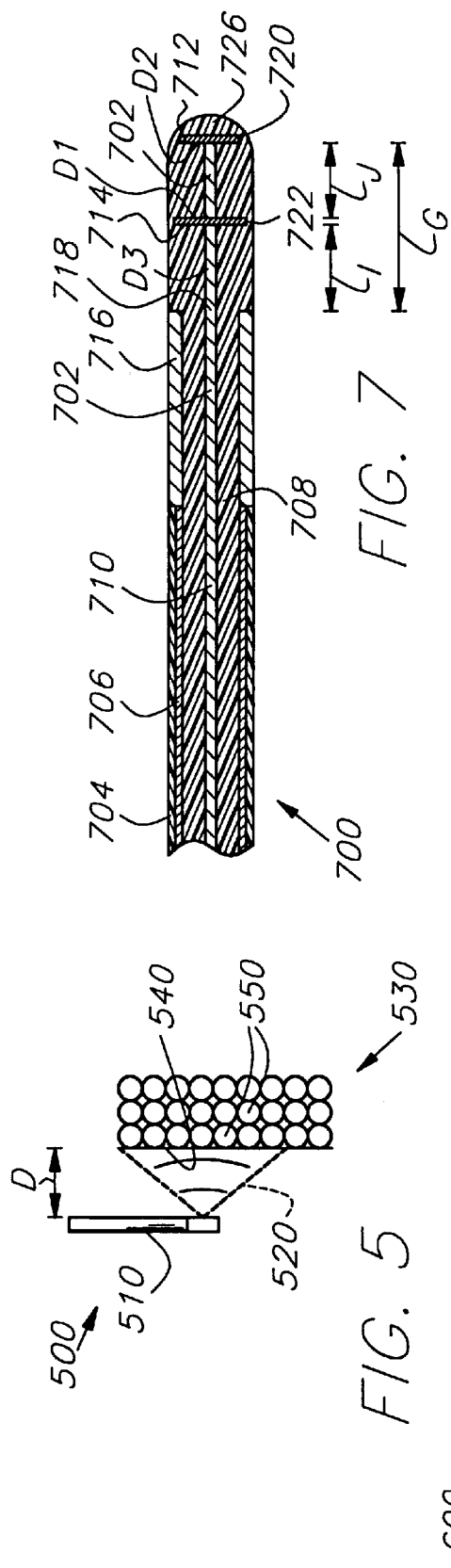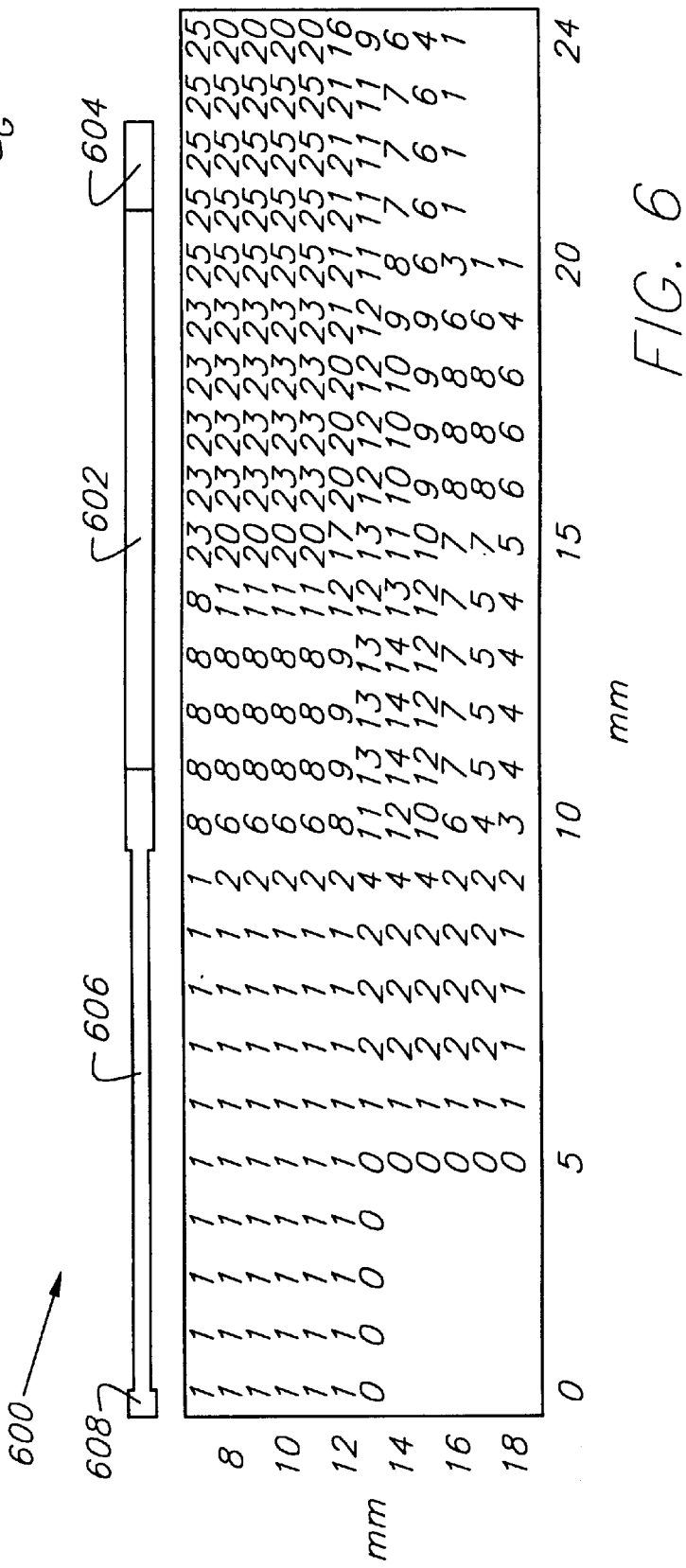

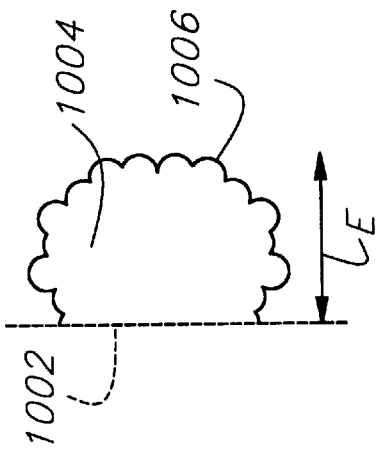
FIG. 10A
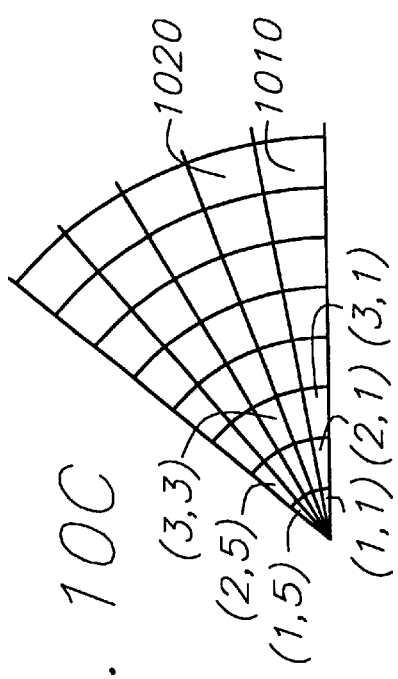
FIG. 10B
FIG. 10C
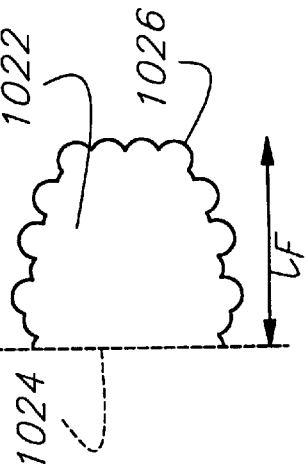
FIG. 11B
FIG. 11A

| GHz | CONDUCTIVITY | | RELATIVE PERMITTIVITY | |
|---|---|---|---|---|
| | HEART | BLOOD | HEART | BLOOD |
| 1.00 | 1.40 | 1.4 | 58.0 | 63.0 |
| 3.00 | 2.70 | 2.7 | 46.0 | 55.0 |
| 10.00 | 8.30 | 9.8 | 37.0 | 45.0 |
| 35.00 | N/A | N/A | 19.1 | 23.6 |
| 1.50 | 1.77 | N/A | 49.0 | N/A |
| 2.45 | 2.21 | N/A | 47.0 | N/A |
| 3.00 | 2.26 | N/A | 46.0 | N/A |
| 5.00 | 3.92 | N/A | 44.0 | N/A |
| 5.80 | 4.73 | N/A | 43.3 | N/A |
| 8.00 | 7.65 | N/A | 40.0 | N/A |
| 10.00 | 10.30 | N/A | 39.9 | N/A |
| 1.00 | 1.30 | N/A | 49.0 | N/A |
| 2.50 | 2.20 | N/A | 45.0 | N/A |
| 8.50 | 8.33 | N/A | 41.0 | N/A |
| 10.00 | 12.50 | N/A | N/A | N/A |

MICROWAVE TREATMENT FOR CARDIAC ARRHYTHMIAS

ORIGIN OF THE INVENTION

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

1. Field of the Invention

The present invention relates to methods and apparatus for propagating a desired radiation pattern of microwave energy into biological tissue, such as heart tissue. More specifically, the present invention relates to control of microwave heating in heart tissue to ablate arrhythmogenic cardiac tissues at depths sufficient to effectively treat arrhythmias such as ventricular tachycardia while preventing injury due to excessive heating of surrounding heart tissues, fluids such as blood, and adjacent organs.

2. Description of Prior Art

Each year more than 100,000 people die of ventricular tachycardia. The survival rate is only 5% for persons who develop this condition.

The medical problem relates to scar tissue that forms on the heart because of a heart attack. Normal heart tissue conducts electrical impulses that fan throughout the heart to produce the heart beat. However, scar tissue may develop or contain regions in which the electrical conductivity is changed from that of normal heart tissue. Under conditions that may develop after months or years following a heart attack, the combination of scar tissue and living cells within the scar tissue may begin to produce undesired electrical impulses. The undesired or abnormal impulses can be produced at excessively fast rates. The abnormal impulses may then fan throughout the otherwise healthy heart to produce the dangerous rapid pumping by the heart ventricles called ventricular tachycardia.

The treatment for this condition is the ablation by some means of the arrhythmogenic cardiac tissues found within the scar tissue. As used herein, ablation refers generally to creating a lesion in the biological tissue that results in a cessation of biological functioning of the remaining living or diseased cells in the scar tissue that disrupt normal cardiac rhythms. For instance, thermal ablation refers to heating cells by about 20° C. to the general range of roughly 57° C. to cause them to cease biological functioning. Once ablated or killed, the cells no longer produce the abnormal impulses that can trigger the rapid increase in heartbeat. However, according to the present invention it is not necessary or desirable to vaporize or char cells for ablation purposes because overheating may cause undesirable side effects.

An additional significant problem of ventricular tachycardia, as compared with other types of cardiac arrhythmias, is that the tissues that produce the abnormal impulses may be found throughout a volume of heart tissue that is relatively deep and wide. The scar tissue may be between 0.5 to 1.0 centimeters in diameter and 1.0 to 2.5 centimeters deep. Effecting the necessary ablation or destruction of the cells throughout the large region is difficult due to the requirement of limiting collateral damage to surface tissues, surrounding tissues, and fluids. In fact, overheating or charring could create new scars that may eventually form new regions of arrhythmogenic cardiac tissues. It is also undesirable to boil or vaporize blood. Yet it is necessary somehow to kill or ablate the cells positioned one to two centimeters below the surface tissue.

Another problem of ablating cells deep below the tissue surface to treat ventricular tachycardia is the difficulty of determining when the cells have been destroyed so that the treatment duration need not be longer than necessary. Stopping treatment when the arrhythmogenic tissue is ablated is desirable to reduce the possibility of complications.

Yet another problem relates to the shape of the scar tissue that may vary significantly from case to case. Besides the above listed problems, providing a means of heating that can efficiently focus on the different shapes of the scar tissue is desirable. Such focussing is desirable to ablate the potentially dangerous cells while avoiding unnecessary damage to healthy heart tissue used to effect normal heart functioning.

Presently, perhaps the most effective long term treatment available for ventricular tachycardia is open heart surgery. During surgery, the diseased portion of the heart is ablated, usually by a cold temperature (liquid nitrogen) probe. However, open heart surgery is so physically stressful that it is not a suitable option for most patients. Furthermore, the cost is high and the recovery period is long and sometimes painful. Therefore, for about 80% of patients, open heart surgery is simply not an option.

Transcatheter ablation effects ablation by means of a catheter that the doctor inserts into the heart through a blood vessel. Due to the potential seriousness of cardiac arrhythmias and the limited number of patients that open heart surgery can help, the development of transcatheter ablation has become an important part of cardiac electrophysiology. Generally, the prior art of transcatheter ablation can be classified as follows:

1) high energy direct current pulses;
2) radio frequency alternating current, typically below 3 Megahertz, that is continuous, pulsed, or a combination of pulsed or continuous;
3) laser ablation that is presently limited to intraoperative ablation;
4) cryoablation; and
5) chemical ablation.

Direct current ablation has been used, with a certain amount of success to treat some types of cardiac tachycardia. However, many problems diminish the utility of direct current techniques. Problems of direct current ablation include limited control of energy delivery and a high rate of serious complications. Also, the lesions so produced tend to be too shallow for treating ventricular tachycardia.

Radio frequency ablation provides much better control of energy delivery and lesion size than direct current ablation. Also, the patient complication rate is lower. However, the lesions are typically shallow and therefore deficient for treatment of ventricular tachycardia. Other problems of radio frequency ablation are discussed in further detail hereinafter.

Laser treatment is presently limited to intraoperative endocardial laser ablation procedures and surgical endocardial resection. The complexity of fiber optic technology and the poor flexibility of the energy delivery systems are the major limiting factors in the use of laser transcatheter ablation.

Cryoablation using catheter delivery is in the experimental stage. Pressurized gas systems have safety and delivery problems. Another disadvantage of cryoablation in the treatment of ventricular tachycardia is that the lesions tend to be small and shallow.

Chemical ablation appears to have many disadvantages for treatment of ventricular tachycardia. The disadvantages include a high complication rate, a high level of potential arrhythmogenesis, a complex delivery system, and significant patient discomfort.

Because of the potential seriousness of the problem of cardiac arrhythmias, numerous inventors have attempted to solve various problems related thereto. For instance, U.S. Pat. No. 4,945,912 to E. Langberg confirms that prior art radio frequency ablation produces lesions that are too shallow for treating some types of cardiac arrhythmias. According to Langberg, previous radio frequency instruments deliver about 10,000 times more energy at the transmitter surface than they deliver in tissues 10 millimeters away, thereby resulting in shallow lesions. A solenoid antenna built according to Langberg to operate at less than 1 Gigahertz would have a heat dissipation ratio at the catheter wall that is only 100 times greater than the heat dissipation in tissues 10 millimeters away. This ratio is a great improvement over the prior art but still leaves ample room for additional improvement. According to the teachings of Langberg, the depth of heating decreases with increasing frequency. Langberg therefore suggests lowering the frequency to obtain deeper heating depths. Subsequent continuation U.S. Pat. No. 5,246,438 to E. Langberg teaches that one reason for decreased depth of heating at higher frequencies is that the electric field for microwave frequency radiation (f>900 Megahertz) attenuates faster due to "skin depth" attenuation.

U.S. Pat. No. 4,641,649 to Walinsky et al. shows a medical procedure for treatment of cardiac arrhythmias using a catheter that includes a flexible coaxial transmission line terminated by an antenna. When the antenna is at the desired location, Walinsky et al. teach to apply radio frequency or microwave frequency electrical energy to the proximal end of the coax to the antenna. The disclosed system uses a 925 Megahertz supply. Walinsky et al. make no further disclosure regarding other frequencies of operation.

U.S. Pat. No. 5,314,466 to Stern et al. discloses an assembly for steering and orienting a functional element at the distal end of a catheter tube. The functional element has a major axis aligned with the axis of the catheter tube for steering to a tissue site.

U.S. Pat. No. 5,281,217 to Edwards et al. reveals a self-cooling coaxial antenna assembly for a catheter that conducts a pressurized cooling medium along the coaxial cable for absorbing heat. While this method is effective, it is also more complicated than a catheter without the cooling assembly. Finding a less complicated cooling system is desirable.

U.S. Pat. No. 5,272,162 to Edwards et al. shows a method and apparatus for contacting a heart valve tissue with a catheter tip electrode adapted for atrioventricular node mapping and modification. The tip is conformed to rest stably and comfortably on a cardiac valve such as the mitral or tricuspid valve.

U.S. Pat. Nos. 5,222,501 and 5,323,781 to Ideker et al. disclose a closed heart method for treating ventricular tachycardia in a heart infarct patient. The method comprises defining a thin layer of spared heart tissue positioned between the heart infarct scar tissue and the inner surface of the myocardium of the patient, and then ablating the thin layer of spared heart tissue by a closed-heart procedure with an ablation catheter.

U.S. Pat. No. 5,295,484 to Marcus et al. discloses apparatus that employs ultrasonic energy delivered to heart tissue to destroy the heart tissue implicated in the arrhythmia.

U.S. Pat. No. 5,172,699 to Svenson et al. discloses an electrophysically guided arrhythmia ablation system for ventricular tachycardia or other arrhythmias. The system combines a recorder, for the electrical activation time of various parts of the heart for finding an active site of the arrhythmia, with an energy delivery apparatus for ablation of the arrhythmia.

I.E.E.E. Transactions on Biomedical Engineering, Vol. BME-34 No. 2, February 1987, by D. M. Sullivan, D. T. Borup, and OM. P. Gandhi, entitled "Use of Finite Difference Time-Domain Method in Calculating EM Absorption in Human Tissues" describes the FDTD method as applied to bioelectromagnetic problems and demonstrates a 3-D scan of the human torso.

I.E.E.E. Transactions on Biomedical Engineering, Volume 35, No. 4, April 1988, by D. Andreuccetti, M. Bini, A. Ignesti, R. Olmi, N. Rubino, and R. Vanni, entitled "Vee and Polyacrylamide as a Tissue Equivalent Material in the Microwave Range", discloses the use of polyacrylamide gel to simulate biological tissues at microwave frequencies.

Other related references include Critical Reviews in Biomedical Engineering, by K. R. Foster and H. P. Schwan, Volume 17, Issue 1, 1989, entitled "Dielectric Properties of Tissues and Biological Materials" and the book "Field Computation by Moment Methods", by R. F. Harrington, MacMillan Press, 1968.

Consequently, there remains a need for apparatus and methods to produce lesions within heart tissue of sufficient size to be useful in treating ventricular tachycardia without damaging surrounding tissues. Also there is a need for apparatus and techniques for customized heat profiles for other arrhythmias and other medical problems that respond to thermal cell injury. Those skilled in the art have long sought and will appreciate the present invention that provides solutions to these and other problems.

SUMMARY OF THE INVENTION

The present invention provides methods and apparatus operable for thermally ablating arrhythmogenic cardiac tissue to treat ventricular tachycardia while controlling the temperature rise in nearby blood and heart tissues. By means of the present invention, raising the temperature of deeply situated arrhythmogenic cardiac tissue by a sufficient level (about 20° C.) without boiling/vaporizing blood or charring/burning surface tissues is possible.

For this purpose, a catheter is provided with a microwave radiator at one end. A frequency of operation is selected between about 1.0 Gigahertz and about 12.0 Gigahertz or higher. The microwave power level of operation is chosen so that a temperature increase from absorption of microwave energy in the blood is limited by the blood exchange rate to a desired temperature range. In tests, the rise in blood temperature adjacent the microwave radiator has been small—less than 2° C. A heating time is determined for the cardiac tissue such that the combination of absorption of microwave energy at the frequency of operation and the thermal conductivity of the arrhythmogenic cardiac tissue and surface blood result in a sufficient temperature rise for thermal ablation of the arrhythmogenic cardiac tissue while controlling blood temperature rise and the maximum temperature in the tissue. The temperature profile varies with frequency, power level, heating time and antenna type. The catheter is positioned to place the microwave radiator adjacent and preferably in contact with the arrhythmogenic cardiac tissue. The microwave radiator will therefore typically be surrounded by blood. A microwave signal of a selected frequency is conducted through the catheter to the microwave radiator at the selected microwave power level for the desired heating time.

Maintaining the frequency of operation of the microwave power between about 2.0 Gigahertz and about 6.0 Gigahertz is generally desirable. This is due to the energy absorption rates at these frequencies for tissues 2 millimeters to 20 millimeters below the tissue surface. To ensure that energy is coupled to the tissues, it is desirable to maintain a standing wave ratio at the antenna input of less than three to one. Preferably, the ratio should be less than about two to one. The catheter may be provided as a coaxial cable structure or a loaded waveguide structure.

The present invention provides a means for providing physical testing of projected results before or after an operation using an apparatus for measuring a transcatheter electromagnetic induced temperature profile within a tissue. The apparatus comprises a tissue receptacle containing therein the tissue that may be actual tissue, animal tissue, or ersatz tissue. The receptacle is preferably substantially water tight along the flow path and defines an inlet port and an outlet port. A pump is provided for pumping fluid, such as saline solution, through the tissue receptacle. Inlet and outlet piping is secured to the pump and secured to respective of the inlet and outlet ports of the tissue receptacle.

A plurality of temperature sensors is disposed within the tissue under test for sensing the temperature profile produced. One or more catheters having an electromagnetic antenna disposed on one end may be used together or separately. A catheter support for supporting the electromagnetic antenna in proximity with the tissue is provided along with a power supply to apply power to the electromagnetic antenna through the catheter. Preferably for accurate testing, the temperature sensors are of a type that is unaffected by electromagnetic transmission such as optical temperature sensors. As well, optical temperature sensor data transmitters such as optical guides are used for relaying temperature data from the optical temperature sensors. A temperature sensor support member may be used for securing the sensor transmission line is a selected position and the support is preferably moveable to allow testing at different size and depth ranges. For the sake of accuracy, the pump is preferably operable for producing peristaltic pumping action. The peristaltic pump used delivers precisely adjustable flow rates. Including a monitor for measuring a standing wave ratio along the catheter is desirable.

Different types of transcatheter microwave antennas can be used with the present invention. Generally, a catheter is provided that comprises a microwave transmission line having first and second opposing ends. The first end is adapted for connection to a microwave power source. The microwave transmission line has a center conductor and an outer conductor. The microwave transmission line has an interior insulator disposed between the center conductor and the outer conductor. The microwave transmission line has an outer insulator in surrounding relationship to the outer conductor. A microwave radiator is disposed on the second end of the microwave transmission line. In one preferred embodiment, the microwave radiator comprises an axial extension of the inner conductor with the axial extension of the inner conductor having a terminal end. The microwave radiator also has an axial extension of the inner insulation material having no outer conductor thereon. It is desirable that a surface wave attenuator be disposed between the microwave radiator and the catheter section. The surface wave attenuator comprises a conductor in surrounding relationship to the inner insulation material. This conductor has no outer covering of insulation material thereon and is electrically connected to the outer conductor.

The radiating element may include an electrically conductive terminal disk electrically connected to the terminal end of the axial extension. Another electrically conductive tuning disk is disposed along the axial extension between the terminal disk and the surface wave attenuator.

A transcatheter microwave antenna for radiating into a blood/heart tissue environment comprises a catheter with a microwave transmission line having first and second opposing ends. The first end is adapted for connection to a microwave power source. The microwave transmission line has a center conductor and an outer conductor. The microwave antenna is disposed on the second end of the microwave transmission line and comprises an antenna conductor extending from the inner conductor and electrically connected to the inner conductor at a feedpoint. An inner insulation axial extension also begins at the feedpoint. The outer conductor ends at the feedpoint that is the beginning of the antenna conductor. A first element radially extends from and is electrically connected to the antenna conductor. A second element radially extends from and is electrically connected to the antenna conductor between the terminal element and the feedpoint. The first element and the second element are spaced at a distance related to tuning the microwave transcatheter antenna between one and twelve Gigahertz.

The transcatheter microwave antenna may also comprise a microwave waveguide having a first and second opposing ends. The first end is adapted for connection to a microwave power source. The microwave waveguide has an outer conductor forming a waveguide and an inner insulative material surrounded by the outer conductor. Terminating the outer conductor to expose an end portion of the inner insulative material forms a microwave radiator at the second end of the microwave transmission. A catheter waveguide may also be used and may have various cross-sections such as round, oval, and the like.

The transcatheter heating method of the present invention can be used to control a temperature profile within a biological structure. The complex dielectric constant of the biological structure may be determined by separate measurements. The thermal conductivity of the biological structure is determined along with its specific heat. The catheter is positioned adjacent the biological structure. A microwave power level may be selected based on the heating constraints of the surrounding regions. A frequency of microwave operation between 1 Gigahertz and 12 Gigahertz is selected for absorption of microwave energy at a desired depth within the biological structure and a heating time is selected to develop the desired temperature profile.

Learning the distance from the microwave radiator to the biological structure is desirable if the microwave radiator is not in direct contact with the surface of the biological structure. Then the complex permittivity, thermal conductivity, and specific heat of any substance, such as blood, disposed within the distance between the microwave radiator and the biological structure can be determined. Determining the amount of reflected energy that will occur at the boundaries or interfaces of transmitter/material and the material/ biological structure is desirable.

Therefore, the present invention provides a method of producing a temperature profile within myocardium (or other heart tissue) when using a transcatheter microwave antenna, comprising steps such as selecting a frequency of operation, selecting a power input, selecting a heating time, selecting a distance from the microwave antenna to a surface of the heart tissue, selecting an antenna with a desired beamwidth, determining a catheter length, determining a complex dielectric constant of the catheter, determining a complex dielectric constant of blood, determining a complex dielectric constant of the heart tissue, determining a thickness of the heart tissue, determining the heat energy deposited within each layer of a plurality of layers of the heart tissue for a desired heating time, determining heat energy transferred by heat conduction within the plurality of layers, and determining the temperature profile within the heart tissue from the total heat energy remaining in the plurality of layers of selected widths of the heart tissue. Plotting a cross-section of a lesion produced in the heart tissue may be desirable. The limits of the lesion may be defined as surrounding the region in which the temperature increase is great enough to ablate cells. As well, finding the lesion cross-sectional area may be desirable. For testing purposes or predictive purposes, it may be desirable to reselect the frequency, and re-compute the temperature profile. Determining the shape of a lesion for ablating arrhythmogenic cardiac tissue may also be desirable. As well, the power input can be reselected and the temperature profile redetermined. Alternatively or in conjunction, the heating period can be re-selected and the resulting effects on the temperature profile re-computed. The effects of the distance between the microwave radiator and heart tissue can be used to re-compute the temperature profile.

A method for controlling microwave radiation into a body tissue environment comprises steps such as providing a coaxial cable with a center conductor and an inner insulator, selecting a diameter for an antenna conductor, and forming a feedpoint where the center conductor electrically connects to the antenna conductor such that the feedpoint is a discontinuity from which microwaves radiate. A plurality of physical discontinuities, such as conductive disks, is provided along the antenna conductor. A distance between the discontinuities is adjusted for tuning the antenna to a desired frequency between one Gigahertz and twelve Gigahertz.

The physical discontinuities preferably include at least two conductive plates electrically connected to the center conductor. Other discontinuities may include changes in antenna diameter, variations in the insulator, center conductor variations, and the like. The diameter of the two plates is selected to provide a bandwidth greater than about one Gigahertz. An insulative sheath is provided around the plates that has a sheath thickness operative for producing a desired bandwidth. Some other features for adjustment include the respective width for each of the two plates, the length of a surface wave antennuator with an antennuator length, and the length of a dielectric end plug length.

A method is provided for radiating a transcatheter microwave antenna with a wide bandwidth in a body tissue environment. The method includes steps such as providing a center conductor for the microwave antenna that extends from a feedpoint of the catheter. The diameter of a first conductive disk secured to center conductor and the insulative sheath surrounding the terminal disk is adjusted for producing a bandwidth greater than two Gigahertz. The thickness of the first conductive disk is selected from a range of between 1.0 millimeters and 2.0 millimeters.

A computer simulated transcatheter method for controlling a radiation pattern into tissues comprises provides a plurality of microwave radiators for producing the radiation pattern. A total electric field is determined at desired positions resulting from the plurality of microwave radiators. The energy is determined at the desired positions in the tissue by determining the energy entering and leaving the desired positions. An isothermic profile produced during a desired time period may be determined. The radiation pattern and isothermic profile may be altered by adjusting a spacing between the plurality of microwave radiators. The spacing between the microwave radiators may be adjusted and the output of one or more radiators may be otherwise controlled. The plurality of microwave radiators may be produced along a single antenna wire.

It is a further object of the present invention to provide a technique for conveniently predicting isothermic region sizes and shapes from power inputs, antennas, frequencies of operation, time duration for heating, and other relevant factors that affect the transfer of heat energy.

Yet another object of the present invention is to provide a test device that allows a close approximation of the actual physical structures within the body by which the various devices and factors can be tested in a realistic setting for purposes such as verifying predicted results, gathering data, refining techniques, and the like.

A feature of the present invention is a transcatheter heating instrument that includes a presently preferred microwave radiator.

Another feature of the present invention is a range of frequencies of operation shown to be especially useful for supplying energy to deep tissues.

Another feature of the present invention is a simulation for determining microwave radiation and the resulting temperature effects in the blood/tissue environment due to impedance discontinuities in a presently preferred antenna caused by physical variations thereof. The microwave radiation mainly comes from three major impedance discontinuities at the antenna feedpoint and at the two conductive disks that connect to the antenna wire.

An advantage of the present invention is the wide range of factors that can be adjusted to consider prediction of future results.

Another advantage of the present invention is the ability to refine techniques both before actual construction and after actual construction of the particular devices to be used.

Another advantage of the present invention is an extremely wide bandwidth antenna that performs optimally with reduced sensitivity to variations such as temperature changes, manufacturing tolerances, operating variables, and the like.

Yet another advantage of the present invention is the ability to tailor and otherwise refine apparatus and/or techniques to the requirements of a particular application. These and other objects, features, and advantages of the present invention will become apparent from the drawings, the descriptions given herein, and the appended claims.

BRIEF DESCRIPTION OF THE DRAWINGS

FIG. 1 is a graph with respect to frequency showing the percentage of energy absorbed in the second to eight millimeters of heart tissue beneath the heart tissue surface;

FIG. 2 is a tabulation showing variation in the volume of heated tissue due to frequency and the maximum temperature within that volume for a selected antenna, power level, and heating time duration;

FIG. 3 is a graph of first and second curves with the first curve showing the percentage of energy absorbed in two millimeters of blood and the second curve showing the percentage of energy absorbed by the first millimeter layer of heart tissue;

FIG. 4 is a graph with respect to frequency showing the percentage of energy transmitted through eight millimeters of heart tissue without being absorbed;

FIG. 5 is a schematic representation of a microwave/thermal simulation model for simulated catheter, blood, and heart tissue;

FIG. 6 is a schematic representation of a temperature profile produced in a beef heart tissue after five minutes of heating as a function of distance along an antenna;

FIG. 7 is an elevation view, in section, of a disk-loaded monopole antenna in accord with the present invention;

FIG. 10A is a numerical tabulation of a projected temperature profile based on selected parameters;

FIG. 10B is a schematic representation of a lesion cross-section from the temperature profile of FIG. 10A;

FIG. 10C is a schematic representation of sections within the temperature profile that shows the relative position of each number tabulated in FIG. 10A;

FIG. 11A is a numerical tabulation of a projected temperature profile developed based on selected parameters varied from those of FIG. 10A;

FIG. 11B is a schematic representation of a lesion cross-section from the temperature profile of FIG. 11A;

While the present invention will be described in connection with presently preferred embodiments, it will be understood that it is not intended to limit the invention to those embodiments. On the contrary, it is intended to cover all alternatives, modifications, and equivalents included within the spirit of the invention and as defined in the appended claims.

DESCRIPTION OF PREFERRED EMBODIMENTS

The techniques of the present invention are designed to achieve deep heating of the ventricular tissue in the lower heart chambers. However, those skilled in the art will recognize that the techniques and instrumentation of the present invention are also suited for other purposes such as heating other types of biological structures.

The desired deep heating parameters of ventricular tissue include a focused lesion size, a penetration depth of 1.0 to 2.0 centimeters, and a temperature rise of 10° C. to 20° C. above normal body temperature with controlled surface and shallow depth heating. The present invention provides a system for development of small, highly efficient antennas for delivering microwave power to create lesions of the necessary size and volume to ablate deeply situated arrhythmogenic heart tissue. The present invention provides development tools including a computer simulation for screening/optimization purposes and a test apparatus for measuring temperature profiles created in tissue surrounded by a simulated blood flow. The present invention therefore even provides the capability and an effective format for continuing evolution of transcatheter antennas.

An ideal microwave system would have (1) minimal heat transferred through the heart into the surrounding organs, (2) minimal heat absorption in the blood and at the surface of the heart, and (3) a uniform heating profile within the region of interest. However, the first condition requires higher frequencies. The second condition requires lower frequencies, and the third condition favors longer heating times to promote thermal conduction. Due to the variety of conflicting operating constraints, computer simulation results are used to predict the isothermal regions.

Figure 8:
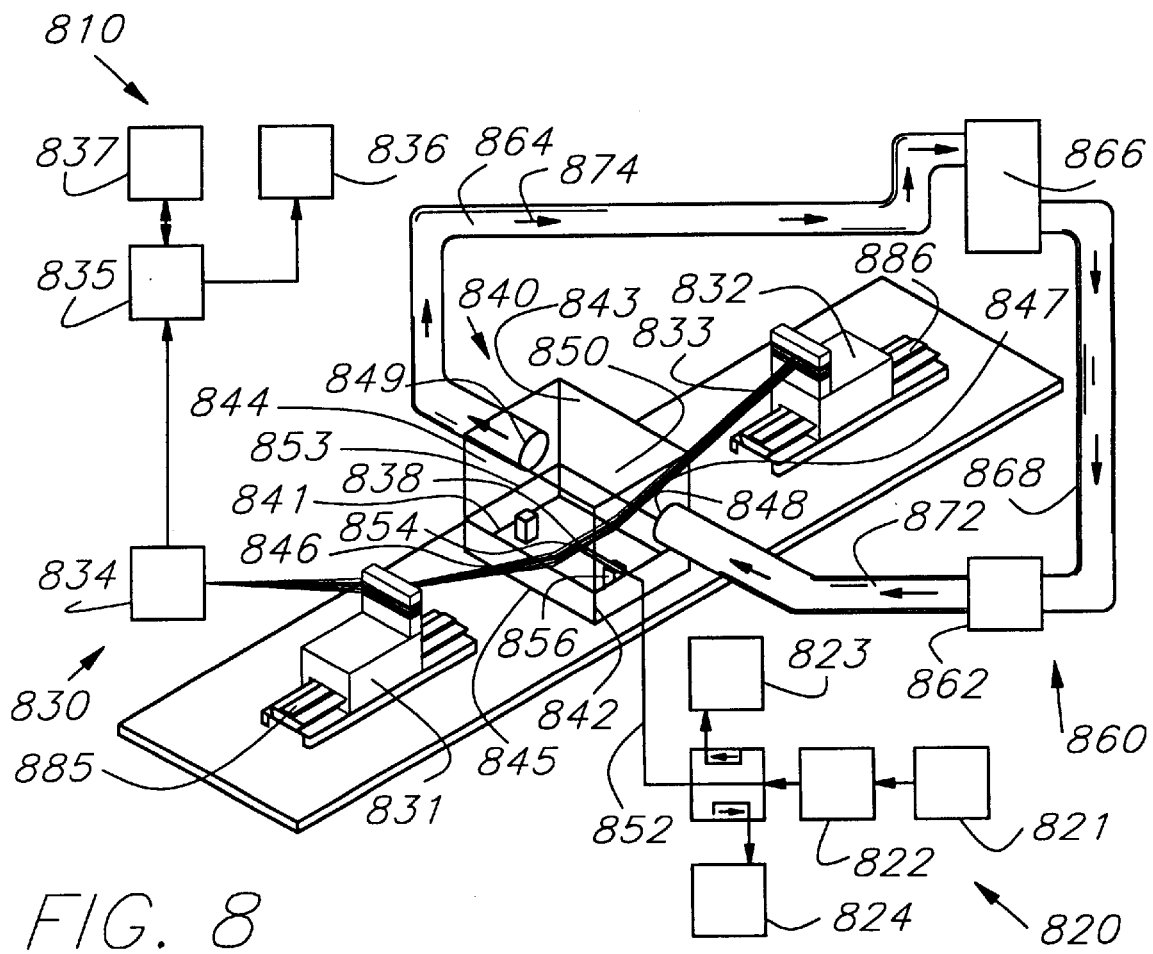
FIG. 8 is a schematic representation of a test setup for temperature profile measurement corresponding to in vivo conditions in accord with the present invention.

A presently preferred range of optimum frequencies for these purposes has been determined from the simulation results. These results will vary slightly depending on values available for simulation input such as conductivity of the heart material at the relevant frequencies. See, for instance, the chart of FIG. 12 that shows conductivity and relative permittivity published data taken from several different sources. It will be noted that the values differ somewhat. A schematic configuration for components of a simulated microwave catheter, referred to as microwave system 500, is shown in FIG. 5. Simulated microwave system 500 is discussed in more detail hereinafter. A schematic representation of a test system for testing promising microwave catheters in a manner that closely replicates in vivo conditions is shown in FIG. 8 and is also discussed in more detail after this. It will be understood that additional research using the tools of the present invention may provide, for instance, more exact operation specifications for frequencies of operation and/or other ranges of frequencies that may be better suited for this or other biological structures such as tumors and the like.

Referring now to the drawings, and more particularly to FIG. 1, there is shown a graph of data represented by curve 10, from a computer simulation in accord with the present invention, that shows the percentage of total energy out of a transcatheter microwave heater absorbed in heart tissues between two millimeters and eight millimeters deep as a function of frequency. The data suggests a broad frequency band, from about two Gigahertz to about eight Gigahertz, that can advantageously be used for depositing significant amounts of energy into deep layers of heart tissue. Frequencies below about one or two Gigahertz tend to partially propagate through the heart muscle with inefficient heating that requires a higher than necessary power level to be delivered through the catheter. Frequencies above about twelve Gigahertz tend to attenuate rapidly resulting in heating primarily at the surface of the tissue. This may be advantageous for some treatments but generally not for ventricular tachycardia.

Figure 14A:
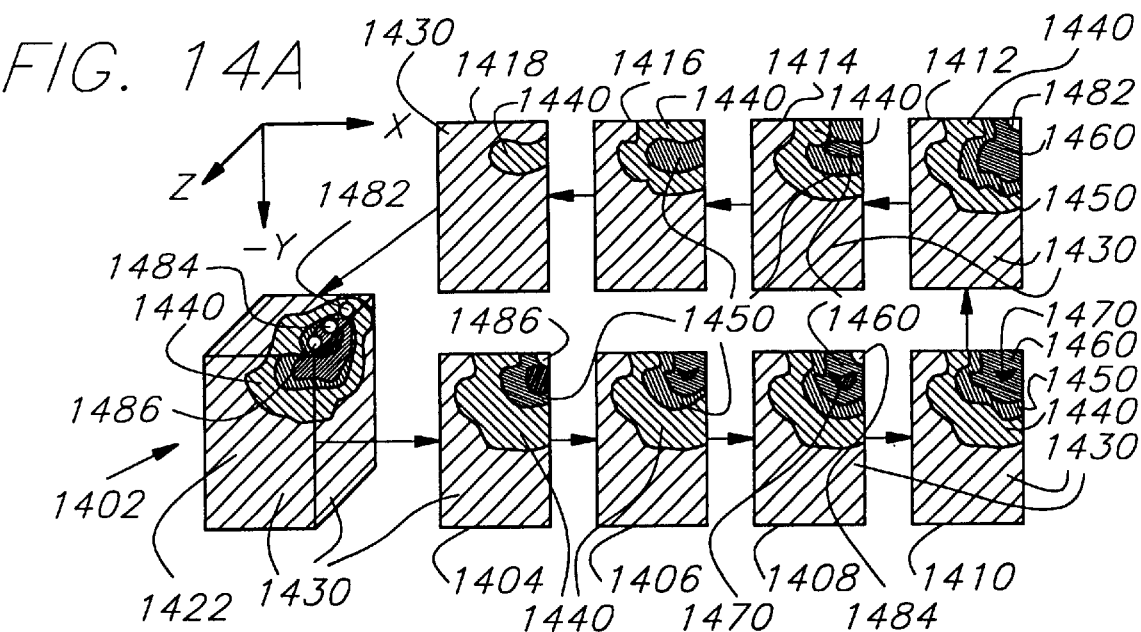
FIG. 14A is a three-dimensional depiction of an isothermic profile produced with a microwave antenna operating at 2.45 Gigahertz and other selected system parameters.
Figure 14B:
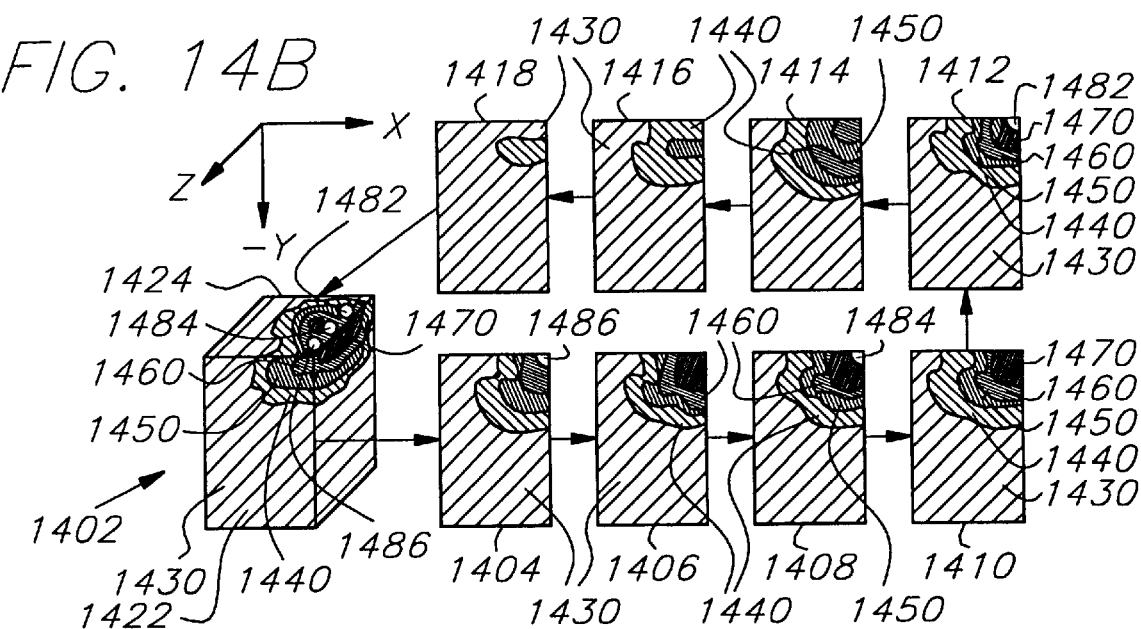
FIG. 14B is a three-dimensional depiction of an isothermic profile produced with the microwave antenna of FIG. 14A operating at 4.45 Gigahertz and based on the same parameters as FIG. 14A.
Figure 14C:
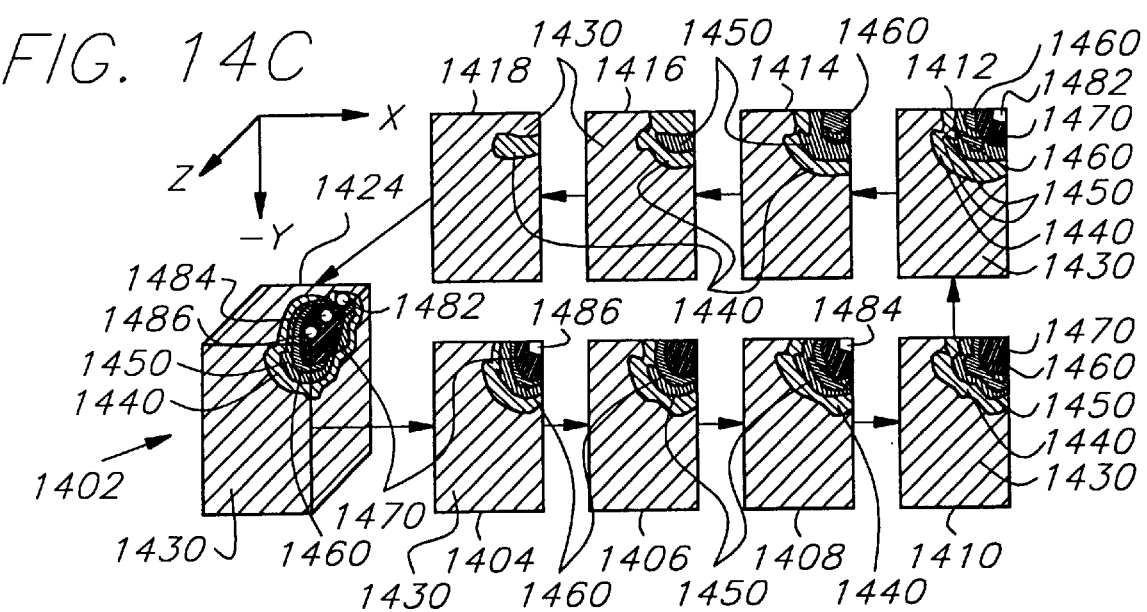
FIG. 14C is a three-dimensional depiction of an isothermic profile produced with the microwave antenna of FIG. 14A operating at 6.45 Gigahertz based on the same parameters as FIG. 14A.

FIG. 2 shows a tabulation of heat effects within a simulated tissue as a function of microwave frequency. For the results of FIG. 2, the power output from the microwave antenna is 14 Watts. The heating time is 6.7 minutes. As discussed hereinafter, the optimal heating time may vary considerably but will probably be between one and several minutes. The simulation results from the chart of FIG. 2 show that for an application frequency of 2.45 Gigahertz, 7583 cubic millimeters of tissue are projected to increase in temperature by more than 10° C. Under the same conditions but at 6.45 Gigahertz, a volume of 4623 cubic millimeters is projected to increase by more than 10° C. As can be seen from the tabulated results, the volume of heated tissue varies considerably as the frequency is changed. This relationship provides the opportunity of matching the lesion size produced to the lesion size required by the patient in the most efficient way. The maximum temperatures created within the simulated tissue is also shown as a function of frequency. The maximum temperatures do not appear at the surface of the tissue because of blood cooling but instead appear one or more millimeters below the surface of the heart muscle contacted by microwave radiator. These general results are discussed more fully in connection with 3-D visual printouts as shown in FIGS. 14A through 14C.

FIG. 3 shows two related curves 310 and 320 plotted as function of microwave frequencies. Curve 310 shows how much energy is projected to be absorbed in two millimeters of blood that radially surround a microwave antenna. Curve 320 shows how much energy is absorbed in the first millimeter of tissue as compared with the total energy that enters the heart tissue. These curves suggest an upper boundary of approximately twelve Gigahertz for utilizable frequency when the energy must pass through a blood layer.

In FIG. 4, curve 410 shows the percentage of the total energy transmitted from a simulated microwave radiator that passes a distance of eight millimeters through heart tissue without being absorbed. To avoid inefficient transmission, the curve suggests a lower bound in a desired frequency of operation for this system of approximately two Gigahertz. For thicker tissue, the lower bound would be at a lower frequency.

In FIG. 7, there is shown microwave antenna or radiator 700 in accord with the present invention. Although many variations of a microwave antenna are possible, double-disk loaded monopole antenna 700 is a presently preferred embodiment of the invention.

Figure 16:
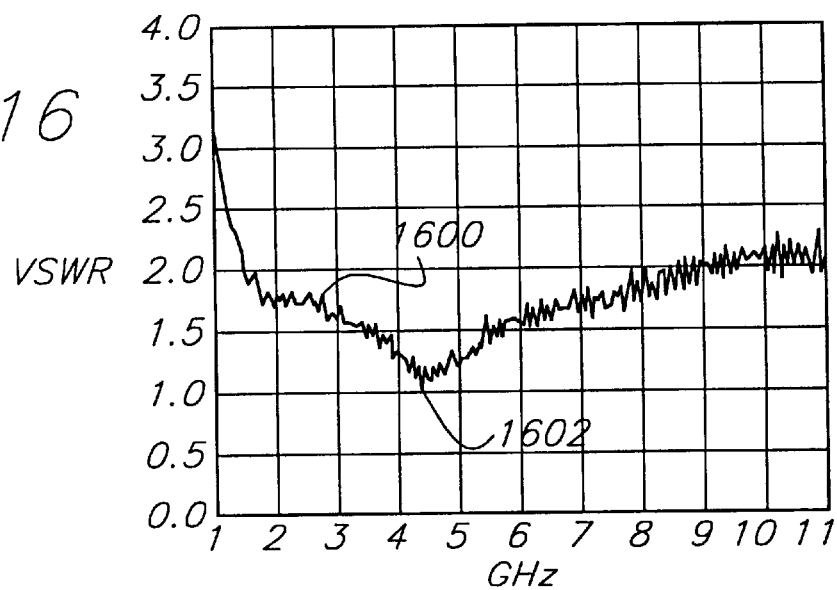
FIG. 16 is a graph displaying the standing wave ratio measured from 1 Gigahertz to 10 Gigahertz for a wideband antenna in accord with the present invention.

Radiation from antenna 700 is primarily concentrated along gap G substantially orthogonal to antenna center conductor 702. In a homogenous environment, the radiation would be radially symmetrical about antenna center conductor or pole 702. In other words, microwave radiator 700 is non-directional and radiates with radial symmetry. Gap G may be varied to increase the beamwidth of the antenna. In a presently preferred embodiment for effecting ablation in myocardium, Gap G is about 0.8 to 1.5 centimeters in length. The double-disk loaded monopole is designed to have a very broad bandwidth so that it can be used over a large bandwidth with little degradation in performance due to manufacturing tolerances or operating environment variations. See, for example, FIG. 16 where the bandwidth for the antenna of FIG. 7 is illustrated in terms of standing wave ratio (SWR) versus frequency. FIG. 16 is discussed in more detail hereinafter.

Insulated jacket 704, that may be comprised of TEFLON or other suitable materials, surrounds outer tubular or cylindrical outer conductor 706. Internal insulator 708 is positioned between outer conductor 706 and concentric inner conductor 710. In some cases as discussed hereinafter, an extension of inner conductor 710 may be used to form antenna pole 702 to thereby simplify manufacture of antenna 700. Internal insulator 708 or other insulative material preferably surrounds antenna pole 702 along its axial length. However, outer conductor 706 and insulative jacket 704 are removed from the region of Gap G to form antenna 700. Two metallic or conductive plates or disks 712 and 714 are preferably physically and electrically connected directly to antenna pole 702. The distance J between the conductive plates or disks is used to tune the antenna over a wide range of frequencies to a very low SWR as illustrated in FIG. 16. The time required for antenna design is reduced by use of antenna design programs as is known to those skilled in the art of antenna design. Such programs include those that calculate finite difference time domain and/or method of moments.

Radiation from an antenna, such as antenna 700, occurs at the discontinuities. Discontinuities in antenna 700 include feedpoint 718, tuning disk 714, and tip disk 712. Since there is little radiation except at the discontinuities, the radiation pattern from antenna 700 can be determined by considering each discontinuity as a separate microwave source. The amplitude and phase relationships can be determined using the finite difference time domain or moment methods. Both were used in designing the present antenna design. The amplitude and phase of radiating points surrounding antenna 700 can be adjusted by such methods as (1) adjustment of spacings such as spacings G, I, and J between the discontinuities, and (2) by adjusting the size of diameters D1 and D2 of tuning disk 714 and tip disk 712, and the diameter D3 of antenna center conductor 702. The complex electric field intensity at any point in the blood/tissue environment surrounding antenna 700 is the complex summation of the three sources or discontinuities at that point. Control of the variables above and others discussed herein changes the radiation pattern and therefore the heating profile. Computer simulations allow manipulation of the variables to obtain the heating profile most similar to that needed.

Antenna 700 is preferably tuned as a broadband antenna as per FIG. 16 where the voltage standing wave ratio (VSWR) is shown by curve 1600 as a function of frequency from 1 Gigahertz to 10 Gigahertz. The wide bandwidth of antenna 700 of the present invention is seen in FIG. 16. There the measured VSWR remains less than two to one from approximately 1.5 Gigahertz to more than 8.0 Gigahertz. Over this entire frequency range, more than 88% of the power is transmitted. For this case, antenna 700 has been tuned for 4.078 Gigahertz as seen at tuning point 1602. At tuning point 1602, the VSWR is 1.065 to 1. Greater than 99% of the power will be transmitted at this tuning frequency. However, for many applications including this one, a two to one VSWR is considered a good impedance match. The advantages of a broad bandwidth include less sensitivity to variations such as temperature changes, manufacturing tolerances, operating environments, and the like.

To obtain a broad bandwidth, diameter D2 of tip disk 712 should be as large as possible. Dielectric sheath 720 surrounding tip disk 712 should be as thin as possible while keeping the total diameter of antenna 700 preferably within 2 millimeters. The same requirements generally hold true for diameter D1 of tuning disk 714 and dielectric sheath 722 surrounding tuning disk 714. Typical values for tuning antenna 700 for a broad bandwidth include making diameters D1 and D2 about 1.8 millimeters and sheath thickness's 720 and 722 about 0.1 millimeters.

The broad bandwidth phenomenon is observable in the design stage of the antenna by using a method of moments computer program. To some extent, the widths of tip disk 712 and tuning disk 714 are also important and can be optimized for best results. By axial positioning of tuning disk 714 between tip disk 712 and feedpoint 718, a precise impedance match can be found between approximately 2 Gigahertz and 4 Gigahertz. See, for instance, point 1602 in FIG. 16.

Conveniently, diameter D3 of center conductor 702 can be made to be the same diameter as center conductor 710 of the 50 ohm coaxial cable if other physical features of the antenna as discussed before are optimized so that inner conductor 710 can simply be extended to form antenna conductor 702. Other dimensions and materials also play a role in matching the antenna. For instance, dielectric end plug 726 is preferably about 1.0 to 3.0 millimeters in axial length. Axial length I from the feed point to tuning disk is preferably about 2.0 to 4.0 millimeters. A preferred value of length J from tuning disk 714 to tip disk 712 is about 2.0 to 4.0 millimeters. The width of tip disk 712, in a presently preferred embodiment, is about 1.5 millimeters. The presently preferred width of tuning disk 714 is about 2.0 millimeters. The length of surface wave attenuator 716 is about 5.0 to 10.0 millimeters. The presently preferred diameter D1 of antenna center conductor 702 is about 0.454 millimeters.

Surface wave attenuator 716 reduces the microwave current flowing back along the outside surface of the catheter. Surface wave attenuator 716 is a metallic ring or tubular electrically connected to outer conductor 706. Surface wave antennuator 716 is uncovered by the outer insulator or TEFLON jacket 704. Reducing surface current is necessary to avoid undesirable heating in the arteries through which the catheter is passed. An antenna 700 in accord with the present invention is therefore operable at high efficiency as discussed hereinbefore for use or testing from 2.45 Gigahertz to 8.0 Gigahertz.

FIG. 5 shows the general design of simulation elements for a microwave radiator system, such as system 500. The simulation is performed by an accordingly programmed computer in which the program may be stored within a storage medium such as a hard disk or disket. The computer effectively acts as a simulator in accord with the programming that may be contained in a memory. Catheter 510 may be either a waveguide or a coaxial cable and represents the first medium through which the microwave energy must travel. Microwave energy 520 emerges from catheter 510 to engage tissue 530. If catheter 510 is not in direct contact with tissue 530, then region D is the distance between the output of catheter 510 and tissue 530 in which blood will be disposed. Therefore, blood will be the second medium through which the microwave energy must travel if the antenna is not in direct contact with the myocardium. Myocardium or other heart tissue or biological structure 530 is the third medium.

In the simulation, the microwave energy travels through surface 540 and heats computation units 550. Each computation unit 550 is one or two cubic millimeters in size in the presently preferred embodiment of the simulation although this size may be varied. The energy applied to these cells by microwave radiation is determined for each selected time increment. As well, the computer computes the energy that leaves/arrives due to thermal conduction for each unit for each selected time increment. In this manner, a computer simulation can determine the temperature profile for the tissue over a total desired heating time that will typically consist of a plurality of short time increments.

The inputs to the simulation include, for instance, the conductivity and relative permittivity of blood and heart tissues at higher frequencies. Conductivity is especially important since the conductivity primarily determines the rate of absorption of the microwave energy into the heart and the maximum propagation distance through the blood and myocardium. As the values of properties such as these become better known, the accuracy of the simulation will increase. Published values for conductivity that are presently available are not in perfect agreement as suggested in the chart of FIG. 12

In a presently preferred embodiment of the simulation, a computational "myocardium" or heart tissue cube having a size that correlates to a region of tissue to be ablated is given the electrical and thermal characteristics of in-vivo myocardium. The cube is subdivided into 8000 small cubes with each cube being a computational cell. The instantaneous heat of one arbitrary computational cell in the cube is given by:

$$Q_c = Q_c^0 + (\Delta Q_{RF} + \int \Delta Q_{HC})\Delta t$$

where:

Q is the new heat energy in the computational cell;

$Q_C^0$ is the previous heat energy level;

$\Delta Q_{RF}$ is the heat added due to absorption of microwave energy;

$\int \Delta Q_{HC}$ is the net heat added or lost by the cell from heat conduction; and $\Delta t$ is a small time constant.

The new temperature of the cell is given by:

$$T_C = Q_C/MS$$

where:

$T_C$ is the new cell temperature in °C.;

M is the mass of the cell; and

S is the specific heat of the cell.

Each cell is assumed to be a cube with six faces. The heat energy transferred through each face for one time increment is given by:

$$\Delta Q = -KA(\partial T/\partial r)\Delta t$$

where:

$\Delta Q$ is the heat transferred through one face;

K is the thermal conductivity of the cell;

$\partial T/\partial r$ is the temperature gradient from the center of one cube to the next; and A is the area of one face.

The electric field intensity in a cell is given by:

$$\hat{E}_1 = \frac{\hat{E}_{01} e^{-\gamma r_1}}{r_1^2}$$

where:

$\hat{E}_1$ is the electric field intensity resulting from the the radiation at the feed point of the antenna; is related to the relative magnitude and phase of radiation from the feed point;

$$\gamma = \alpha + j\beta;$$

α is the attenuation constant associated with the tissue;

β is the phase shift constant; and $r_1$ is the distance from the antenna feed point to the center of a cell.

The total electric field at a cell due to radiation from the feed point, middle disk and top disk (each being a microwave radiator) is given by:

$$\hat{E} = \hat{E}_1 + \hat{E}_2 + \hat{E}_3$$

where:

$\hat{E}_2$ is calculated similarly to $\hat{E}_1$ except using $r_2$ to the mid-disk; and $\hat{E}_3$ similarly uses $r_3$.

Finally, the energy absorption at the cell is given by:

$$W_a = v\sigma|E|^2 \Delta t$$

where:

$W_a$ is the electromagnetic energy absorbed;

v is the volume of the cube; and

σ is the conductivity of the medium.

The results from the simulation can be plotted in many ways to show the size and shape of the projected isothermal volumes. As an example only, FIGS. 14A, 14B, and 14C show the effect of choice of frequency on the isothermal contours projected to be created within the myocardium or other heart tissue. In FIG. 14A, the chosen frequency is 2.45 Gigahertz. In FIG. 14B, the chosen frequency is 4.45 Gigahertz. Finally, in FIG. 14C, the chosen frequency is 6.45 Gigahertz. In each simulation, the antenna radiated power is 14 watts. The simulated antenna used in each trial was of similar construction as antenna 700 described in connection with FIG. 7. In FIG. 14A, the power is applied to the antenna for 401 seconds. The energy deposited in cube 1402 of myocardium by the end of the run is 1102 joules. In FIG. 14B, the power is applied for 321 seconds and the energy deposited is 875 joules. In FIG. 14C, the power is applied for 429 seconds and the energy deposited is 784 joules. In each case, the instantaneous power being absorbed at the end of the run is one watt.

FIG. 14A through FIG. 14C each show a solid cube 1402 of myocardium and eight respective x-y cross-sections 1404, 1406, 1408, 1410, 1412, 1414, 1416 and 1418 taken along the z-axis of cube 1402. The x-y cross-section 1404 is taken from front 1422 of cube 1402 and x-y cross-section 1418 is taken from rear side 1424. A large portion of cube 1402 is removed and the remaining volume is partially displayed in phantom to more clearly show the isothermal zones. More specifically, half the original cube 1402 is cut away in the x-axis direction and half is cut away in the z-axis direction.

In FIGS. 14A–C, the isothermal zones of temperature ranges are shown by the respective shading. In a presently preferred embodiment, these zones may be represented by different colors. Isothermal zone 1430 represents the zone in which the projected temperature change is less than 10 degrees Kelvin. Projected isothermal zone 1440 represents a change greater than 10 degrees but less than 20 degrees Kelvin. In all the remaining isothermal zones, the projected temperature change is greater than 20 degrees Kelvin so that it can be predicted that substantially all cells are ablated in these zones. In projected isothermal zone 1450, the temperature change is greater than 20 degrees but less than 30 degrees Kelvin. The temperature change in isothermal zone 1460 is more than 30 degrees Kelvin but less than 40 degrees. Finally, in isothermal zone 1470, the temperature change is greater than 40 degrees Kelvin.

In this simulation, the catheter and antenna are laying on top of cube 1402 of the myocardium and are parallel to the z-axis. The feedpoint, central disk, and tip disk (see discussion of FIG. 7) are depicted by small white circles 1482, 1484, and 1486, respectively, in cube 1402 and are also shown at to top right in x-y cross-sections 1404, 1408, and 1406.

For the simulation of FIGS. 14A, 14B, and 14C the respective conductivity values in mhos per meter of the simulated myocardium are 2.56 mhos/m, 4.12 mhos/m and 6.45 mhos/m. The respective attenuation constants in decibels per meter are 569 db/m, 928 db/m, and 1474 db/m. The thermal conductivity used in all three is 0.00143 cal/sec-°C.-cm. The phase change in the signal from the feedpoint to the end disk for the three simulations is, respectively, 34.08622 degrees, 61.91171 degrees, and 89.7372 degrees. By comparing FIGS. 14A, 14B, and 14C, it can be seen that the volume of myocardium having at least a 10° C. temperature increase is greatest at 2.45 Gigahertz or at the lowest of the three frequencies. The volume of myocardium with at least a 10° C. increase is smallest at 6.45 Gigahertz. It should be noted that for short time durations, the opposite occurs.

For the simulation conditions, the blood temperature at the surface of the myocardium rises with increasing frequency. The maximum temperature in the myocardium moves to shallower depths with increasing frequency. Also, the maximum temperature produced in the myocardium increases with frequency. Thus, as seen in FIGS. 14A through 14C, the heat contours or isothermic zones can be customized by choice of frequency. Further customization can be produced by selecting power level, duration of power delivery, and antenna type. As an alternative embodiment of the present invention, the program may be altered to accept the desired heat contours as the input. By working backwards from a desired thermogenic profile, the program could be used to select the most appropriate choice of frequency, power level, duration of power delivery, placement of discontinuities in the antenna and other factors as discussed herein.

Figures 15A, 15C:
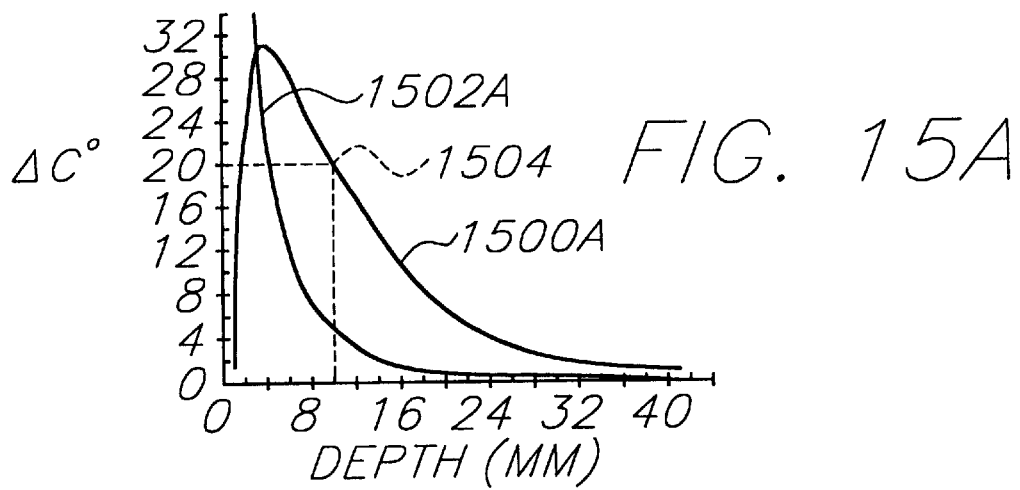
FIG. 15A is a graph showing the relative microwave absorption rate profile and equilibrium temperature profile in water at 2.45 Gigahertz.
FIG. 15C is graph similar to that of FIGS. 15A and 15B except for a frequency is 6.45 Gigahertz.
Figure 15B:
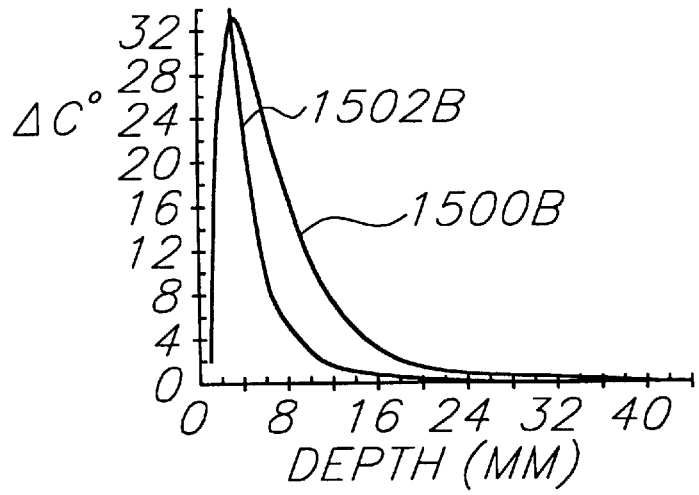
FIG. 15B is a graph similar to that of FIG. 15B except for a frequency of 4.45 Gigahertz.

FIGS. 15A, 15B, and 15C show equilibrium profiles and energy absorption rate profiles in a water medium for the same frequencies as used in FIGS. 14A, 14B, and 14C. Thus, the trial depicted in FIG. 15A was performed at 2.45 Gigahertz, FIG. 15B at 4.45 Gigahertz, and FIG. 15C at 6.45 Gigahertz. Note that the absorption rate profile, indicated by respective curves 1500A through 1500C in each FIGS. 15A–15C, becomes steeper as frequency is increased. This results in the peak temperature moving to shallower depths when thermal equilibrium is reached. In FIG. 15A, it will be noted that at point 1504, a change in temperature of 20° C. is produced at a depth of about 10 millimeters. The maximum temperature change of 31° C. in the trial of FIG. 15A is produced at a depth or radial distance from the antenna of about four or five millimeters. FIGS. 15A, 15B, and 15C were produced using water as the material surrounding the antenna but the curves are generally representative of what occurs in blood and in vivo myocardium. Six thousand cubic millimeters of water were used as the environment in each of these three tests. Respective power pulse 1502A–1502C in each of these three trials has a duration of 600 seconds. The antenna power output for each trial is about seven watts.

Due to changes in frequency, the amount of energy deposited into the water varies. In the trial of FIG. 15A, 304 joules are deposited. In the trials of FIGS. 15B and 15C, 350 and 360 joules, respectively, were deposited.

An alternative embodiment of the computer simulation of the present invention uses relationships as discussed below. The alternative embodiment provides a significant amount of information concerning the possibility of different types of materials or mediums being disposed between the antenna and the desired target tissues such as heart tissues or other biological structures. In the presently preferred operating embodiment, the antenna is preferably placed against the heart tissue. However, an additional medium could be interspersed between the antenna and the tissue such as a thin layer of blood as when the antenna is not in direct contact with the heart tissue. Moreover it has been noted several times hereinbefore that the present invention could be used in different applications that might include one or more different types of mediums or tissues between the antenna and the tissues to be heated, e.g., heating of tumors or other abnormalities in the prostate, ovaries, intestine, and the like.

In this alternative embodiment of the computer simulation, the power attenuation of an electromagnetic wave at a specified frequency is given by:

$$W = w_o e^{-2\alpha d}$$

where:
W=power density in watts/meter;
$w_o$=original power density;
$\alpha$=attenuation coefficient of the medium in nepers/meter; and
d=the distance traveled through the medium.

The fractional power absorbed by one thin layer (preferably one millimeter thick):

$$L = 1 - e^{-2\alpha l}$$

where:
L=the fractional power lost in the layer; and
l=one thin layer of the medium (preferably one millimeter 0.001).

Then the power into the heart muscle (the third medium) is:

$$P_3 = w_2(1-|S_{22}|^2)A_c$$

where:
$P_3$=power into the heart muscle;
$w_2$=power density incident at the blood/heart interface;
$A_c$=area of one computational unit or cell; and
$S_{22}$=electric field reflection coefficient at the blood/heart interface.

The reflection coefficient is given by:

$$S_{mm} = (\eta_m - \eta_n)/(\eta_m + \eta_n)$$

where:
$S_{mm}$=the electric field reflection coefficient;
$\eta_m$=the intrinsic impedance of the medium before the interface;
$\eta_n$=the intrinsic impedance of the medium after the interface; and
m=the medium after the reflecting interface.

The relationship for intrinsic impedance is given by:

$$\eta = j\omega\mu/(j\omega\mu\sigma - \omega^2\mu\epsilon)^{1/2}$$

where:
$\omega = 2\pi f$=radian frequency;
$\mu$=permeability of the medium;
$\sigma$=conductivity of the medium;
$\epsilon$=permittivity of the medium; and
$j = -1^{1/2}$ The power to energy conversion relationship:

$$J = P_d T$$

where:
J=joules;
$P_d$=power dissipated in watts; and
T=time of delivery.

Electrical energy to heat energy is given by:

$$\Delta Q = J * 4.182$$

where:
$\Delta Q$=the calories added.

The heat rise in a computational cell or unit is:

$$\Delta T = \Delta Q/mc$$

where:
$\Delta T$=temperature increase in degrees Centigrade;
m=mass of a computational unit or cell in grams; and
c=the specific heat of the heart muscle in cal/(gram—°C.).

Heat conduction is given by the equation:

$$\Delta Q = -k A_c (\Delta T/\Delta l)$$

where:
k=thermal conductivity in watts/meter −°C.; and
$\Delta T/\Delta l$=the thermal gradient in °C. per meter.

The following inputs are used. Many of them remain constant from test to test. The first five inputs may be changed more often depending on the system to be analyzed.

Frequency of operation in Gigahertz;
Power Input in watts;
Length of heating period in seconds;
The Distance from the Antenna to the heart wall in meters;
The Beamwidth of the Antenna in degrees;
The radius of the waveguide or coaxial cable;
The length of the waveguide or coaxial cable;
The increment time for updating each computation;
The computation unit or cell size;
The relative dielectric constant in the waveguide or coaxial cable that comprises the first medium through which the microwave signal travels;
The loss tangent or conductivity in the waveguide or coaxial cable;

The relative dielectric constant of the blood that is medium two;

The loss tangent or conductivity of the blood;

The relative dielectric constant of the heart muscle or heart tissue generally that comprises medium three;

The heart muscle thickness;

The desired lesion radius;

The loss tangent or conductivity in the heart tissue or heart muscle that comprises medium three;

The thermal conductivity of blood;

The thermal conductivity of the heart;

The specific heat of the heart;

The density of the blood; and

The density of the heart muscle.

From the inputs given hereinbefore, additional inputs are determined using the equations from above where applicable. Note that sometimes, these values may also be given or already known rather than calculated or measured.

Determine the impedance of each medium.

Determine the required relative dielectric constant in the waveguide or coaxial cable.

Determine the voltage in the waveguide or coaxial cable and the dielectric strength that it requires.

Determine the power out of the waveguide or coaxial cable.

Determine the directivity of the antenna.

Determine the power density into medium two (blood).

Determine the losses in medium two.

Determine the reflected energy at the interface of medium two and medium three.

Determine the power into the heart tissue.

Once the above items are known, then the energy absorbed within the heart can be determined by making calculations for each computational unit or cell and for each time increment.

Determine the power into layer one of the computational units or cells.

Determine the energy deposited by heat conduction to adjacent computational cells.

Compute the heat remaining in the cells of layer one.

Compute the temperature rise in °C. in layer one.

Repeat this procedure for layers two through layer N.

Increment the time by the time increment.

Repeat the steps above until the heating time is completed, until the maximum temperature is reached, or until another desired event occurs.

The results from the simulation can be plotted showing lesion size, shape and temperature profile. It will be understood that the data can be displayed or otherwise output in many different ways that may enable clearer understanding of the results.

In FIG. 10B, a cross-sectional plot is provided that shows the shape of simulated lesion 1004 defined as the region in which the temperature was increased by about 20° C. such that one could expect ablation of cells. The frequency of operation is six Gigahertz for this trial simulation, the heating time is twenty-five seconds, and the power applied is twenty watts. The simulation of the present invention can be used to obtain the three-dimensional isotherms providing the lesion shape and size. The views can be projected from any desired orientation. Distance or depth E into the heart tissue is measured from the heart tissue surface 1002 and is the maximum depth of the lesion created as defined by a 20° C. increase in temperature indicated by outline 1006. Here, the maximum depth E is about seven millimeters.

The tabulation of FIG. 10A shows the temperature profile, as degrees increase above normal body temperature, going into the tissue. The tabulation of FIG. 10A correlates with the cross-sectional view of FIG. 10B. FIG. 10C shows a radiation pattern divided into cells so that the position of each cell correlates with a temperature of the tabulation of FIG. 10A as discussed hereafter. Each row or wedge 1010 or 1020 in FIG. 10A represents an additional 10 degrees of the radiation pattern from the simulated antenna. The antenna would be found at the apex of the wedge. The mirror image of the graph is not shown and would extend downwardly. Therefore, it is understood that the actual pattern is about twice the size shown.

In this simulation, it is assumed that the first two rows including cells (1,1) through (5,1) and (2,1) through (2,5) occur in the blood between the antenna and the heart tissue surface. Each row represents one millimeter and there are two millimeters of distance between the antenna and tissue surface 1002. The tabulation of FIGS. 10A and 11A start at the tissue surface. The tissue surface begins at cell layer (3,1) through (3,5). It will be understood that the simulation could be made with the antenna engaging tissue surface 1002 or with other spacings or biological materials, if desired.

The third row of FIG. 10A, comprised of units (3,1) through (3,5), is represented by the first column of FIG. 10A. The tabulation of FIG. 10A shows the temperature for each section of the radiation pattern of FIG. 10C. For instance, computational unit (3,1) is in the first millimeter layer of heart tissue and the temperature increase shown for that unit in the tabulation of FIG. 10A is 41° C. Each subsequent number along the bottom row of the tabulation of FIG. 10A shows the temperature one additional millimeter going into the tissue. At computational unit (3,3), which unit also lies on the surface of the tissue, the temperature increase is 36° C. and is about twenty degrees offset from the heart tissue at computational unit (3,1). As can be seen from the tabulation of FIG. 10A for this simulation, ablation of cells about seven millimeters deep would be probably be suggested because the eighth cell has a 19° C. increase over normal body temperature.

In the simulation of FIG. 11A, the frequency of operation is two Gigahertz, the heating time is fifteen seconds, and the power applied is twenty-five watts. The shape of the cross-section of the lesion is shown in FIG. 11A. Again, a lesion such as lesion 1022 is formed as shown in FIG. 11B. Maximum depth F that extends from tissue surface 1024 to the maximum depth of lesion 1022 is at least eight centimeters deep as can be seen more clearly from the tabular printout of 1A. Outline 1026 is altered due to the variation in parameters as shown. The printout of the shape of lesion 1022 could also be shaded to show gradations of temperature if wanted.

FIGS. 10B and 11B are shown as examples only. Many variations may occur in the shape of the lesions as the variables are changed. Furthermore, it will be understood that many different options can be used for printout formats. For instance, the results of multiple simulations and the basis for the comparison between the simulations can be plotted. Variables besides frequency, power, and time could also have been altered to determine their effect on lesion shape if desired. Variables may include the distance between the radiator and the tissue surface, the power levels, the radiator beamwidth, the results of a reflector or other means to direct the microwave beam, and the like. The inputs for the simulation can be used to describe a variety of antennas as wanted although simply the beamwidth of an antenna will provide significant information.

The equations used to determine the energy absorbed can be varied as necessary to describe any unusual type of electromagnetic wave projection that may be used if necessary and assuming the mathematical expression is known or can be determined. Thus, the computer simulation of the present invention provides a means for initial screening of many different antennas and techniques for applying heat to the heart muscle. As well, the computer simulation of the present invention can be used to refine an antenna or technique of operation that already shows significant promise. Furthermore, the computer simulation can be useful for adapting to characteristics of particular patients such as muscle thickness, lesion size and shape, and other factors that may vary from patient to patient.

Referring now to FIG. 8, test setup 810 is shown that is used to measure temperature profiles under conditions that are comparative to the temperature profiles anticipated during actual in vivo use within the human body. The primary components of test setup 810 include power generation and monitoring equipment 820, fiber optic heat profile measuring system 830, tissue receptacle 840, catheter 852, antenna 854, and fluid movement system 860.

Tissue receptacle 840 is preferably at least partially water tight to hold saline solution pumped through tissue receptacle 840 to simulate blood flow as discussed hereinafter. Tissue 841 is positioned along a bottom portion of tissue receptacle 840. Tissue 841 may be ersatz heart tissue or it may be actual heart tissue such as beef heart tissue that is readily available at certain grocery stores and the like. The ersatz heart tissue is convenient to work with, inexpensive, plentiful, and used at least for preliminary testing. For measurements taken at 2.45 Gigahertz, ersatz heart material was used that included 8.46% TX151 gelling agent, 15.01% polyethylene powder, 76.03% deionized water, and 0.50% reagent grade salt.

Although other combinations of material may be used, these have been found to simulate the complex permittivity of the heart muscle at the desired frequencies of testing. The recipe must be modified for other microwave frequencies. Preferably, the complex permittivity of the gelatin should be measured, as with for instance a HP85070B probe and an HP8510B network analyzer. Such instruments are also useful to measure the complex permittivity of the beef heart, blood, and saline solution. The thickness 842 of the ersatz heart material in the tester is preferably at least two inches.

In the presently preferred embodiment, tissue receptacle 840 has dimensions of 6"×6"×10" and is comprised of lexan ¼" thick walls such as walls 843, 844, and 845. For convenience in test setups, receptacle 840 is open at top 850. Arrays of holes 846 and 847 are used for fiber optic temperature sensor access into heart material 841. Inlet 848 and outlet 849 are used to allow the pumping of saline solution 872 through tissue receptacle 840.

Power generation and monitoring equipment 820 include signal generator 821 that may produce different types of signals as wanted. In this setup, signal generator 821 may be used to produce continuous wave signals, the duration of which is timed manually. However other signal generators may be used to produce signals such as pulsed signals, variable duty cycle signals, and the like, for testing as wanted. Amplifier 822 amplifies the signal produced by signal generator 821 to the desired wattage power level. One embodiment of the invention uses a twenty-watt amplifier although more or less powerful amplifiers could also be used. The amplifier may have an adjustable output so that power output may be adjusted to account for differences in impedance matching as may be needed for making tests more uniform with respect to the power radiated by the antenna. Incident wave power meter 823 and reflected wave power meter 824 allow the determination of the standing wave ratio (SWR) of the signal. This ratio provides an indication of the efficiency of the system for coupling the microwave signal power through the different mediums of the catheter, blood, and finally to the tissue where it is desired to deposit the heat energy. It is desirable that the SWR be in the general region of less than about three to one and most preferably less than about two to one. One way the operator, doctor, or computer control (not shown) can tell that power is delivered appropriately will be to monitor the SWR or some indicator for the SWR.

A fiber optic heat measurement system, such as system 830, avoids electromagnetic interference and related measurement inaccuracies that would be created with a metallic heat measurement system. Fiber optics heat profile measurement system 830 includes left positioner 831 and right position 832 that support twelve fiber optic cables 833 containing therein optical heat sensors 838 in the desired position for temperature profile measurement purposes within the heart tissue. Positioners 831 and 832 preferably include rails 885 and 886, respectively, that allow convenient means for fixing relative placement.

In one series of tests the sensors were positioned at a 4.7 millimeter depth, a 7.7 millimeter depth, and a 10.7 millimeter depth. In other tests, other depths were used such as an 11.0 millimeter depth, 14.0 millimeter depth, and 17.0 millimeter depth. The fiber optic cables can be adjusted within arrays of holes 846 and 847 to change the depths of measurement and to change the position of the sensors compared with antenna 854. Antenna 854 is oriented by support 856 so its longitudinal axis is preferably exactly perpendicular to the orientation of optic cables 833. Antenna 854 also preferably engages surface 853 of tissue 841.

Catheter 852 electrically connects between power generation system 820 and antenna 854. Catheter 852 may be a coaxial cable or a waveguide. Catheter 852 is selected to be suitably flexible for insertion through a vein. It can handle at least 20 watts of power and is preferably about 2 millimeters in diameter so as to be insertable through a vein or artery.

The signals from optic cables 833 are detected in optical scanner 834 where they are multiplexed and applied as electrical signals to computer 835. Outputs from computer 835 may be to color printer 836 or monitor 837. The outputs for the test results may be presented in many different formats just as the results of the computer simulation discussed hereinbefore. For instance, the various temperatures may be color coded for a color presentation of the measured temperature profile produced with color printer 836.

Fluid movement system 860 includes pump 862, receptacle outlet pipe 864, reservoir 866, reservoir—pump pipe 868, receptacle inlet pipe 870, and fluid 872 that flows in the direction of arrows 874. A saline solution, with the electrical properties adjusted as necessary, simulates blood flow. The flow rate of pump 862, the volume of reservoir 866, the diameter of inlet and outlet pipes 872 and 864, respectively, and the like, can be adjusted to account for heat removal caused by blood flow. Pump 862 is preferably operable or selectively operable for pumping with peristaltic action to simulate heart pumping action.

FIG. 6 shows the measured temperature profile, from the system of FIG. 8, in a beef heart plotted as a function of distance along the antenna and depth into the tissue. This data is for an operating frequency of 3.45 Gigahertz and a heating time of five minutes. Heating is shown in a two-dimensional plane that is perpendicular to antenna 600. Antenna 600 is a monopole antenna like antenna 700 with gap 602 being one centimeter in length and ending with a tip disk at end 604. The approximate position of the tuning disk (not shown) can be determined from the printout. Surface wave attenuator 606 is positioned adjacently to gap 602 and is connected to coaxial cable catheter 608. Although surface wave attenuator 606 is shown having a smaller diameter than coaxial cable 608 this may or may not be the case according to the specific design. The number grid below the antenna shows yet another format for displaying a temperature profile. The chart provides the temperature for each square millimeter unit except that the six millimeters closest to the antenna are not displayed. For instance, it can be seen that 12 centimeters radially outwardly from antenna gap 602, the temperature increase was 20° C. as read between the bottom scale millimeters 16 and 19. Therefore, this antenna would have effectively ablated cells to at least 12 centimeters deep in the tissue without charring surface tissues or boiling blood. At 13 centimeters radially outwardly from gap 602, the temperature drops suddenly. Thus, although the lesion is quite deep, the heat would be unlikely to harm the surrounding tissues because the focus of the antenna is so well controlled.

Figures 12, 13:
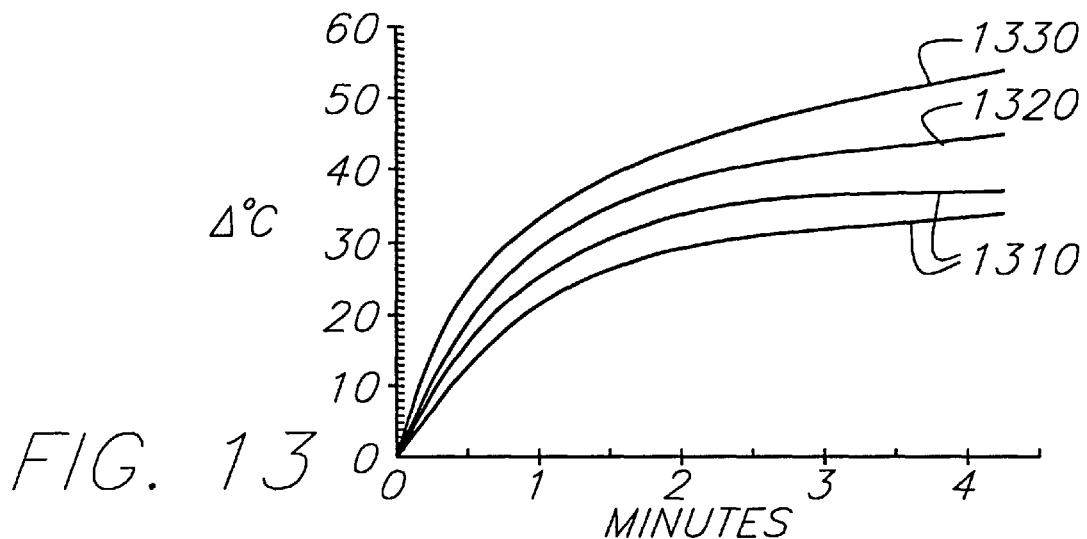
FIG. 12 is a chart showing heart and blood conductivity and relative permittivity from different references versus frequency above 1 Gigahertz.
FIG. 13 is a chart with respect to time showing temperature increases at various depths within ersatz heart material.

FIG. 13 shows a typical heating profile for the ersatz heart material used in the system shown in FIG. 8. Curves 1310 are readings from sensors positioned at 4.7 millimeters from the surface of the ersatz heart material. Curves 1320 are from sensors at 7.7 millimeters depth. Curves 1330 are readings from a 10.7 millimeter depth. The output wattage from the antenna is 7.48 watts. The heating time (time the power was on) is about 3.75 minutes. The frequency of operation was 3.95 Gigahertz and the gap length of the antenna was one centimeter. The antenna was disposed on top of the ersatz heart material and immersed in saline solution. Several results of such tests may be summarized as follows:

1) The rate of temperature increase at shallow depths quickly levels off due to the cooling effect of the saline solution such that at equilibrium the energy into these tissues equals the energy out of the tissues.

2) The deeper temperatures do not level off as rapidly but instead continue to increase with time. They are not as affected by the cooling of the circulating saline solution at the surface. Heating is a combination of electromagnetic heating and heat conduction from the shallower depths. It is useful to note that the deeper heating is almost a linear function of time for up to several minutes. In other words, a 7.0° C. rise after 90 seconds would be approximately 14.0° C. after 180 seconds. This fact may be a handy rough guide when calculating how long heating should continue.

3) The deep heating is also essentially a linear function of the microwave power radiated by the antenna for at least several minutes.

By using knowledge of simulated tests either by computer or by physical testing, the heating time required may be predicted to ensure ablation of the desired region even at significant depths while preventing unnecessary additional heating. Real time computer monitoring and analysis may also be used where possible to make more accurate judgments of heating time based on factors that may not always be predictable or that may change such as SWR, changes in procedures due to contingencies, and the like. If multiple catheters are used, computer monitoring may also be desirable. Multiple catheters may be used to provide sensor information or be used for additional heating if required.

Figure 9A:
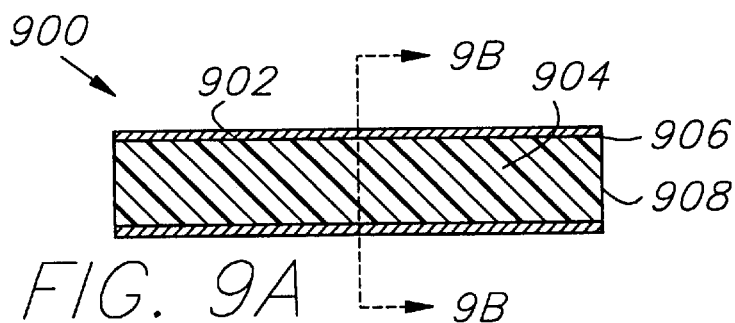
FIG. 9A is an elevational view, in section, of a catheter waveguide for a microwave radiator in accord with the present invention.
Figure 9B:
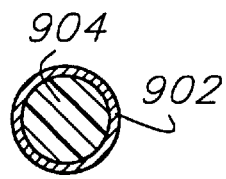
FIG. 9B is an elevational view, in section, along the line 9B—9B.

Although coaxial cables have been discussed hereinbefore, waveguides could also be used as shown in FIG. 9A. Waveguide 900 comprises outer conductor 902 and inner dielectric material 904. Since the cutoff frequency within a loaded waveguide is inversely proportional to the square root of the dielectric material within the guide, a 12 Gigahertz signal in a 2 millimeter waveguide requires a relative dielectric constant of about 80. A circular cross-section waveguide 900 may be used as shown in FIG. 9B but it may also be desirable to have an oblong, ovate, or other cross-section in some cases. By providing terminating ends 906 and 908 of waveguide 900, a microwave radiator is formed. In some ways, waveguide 900 may be easier to position in the heart chamber correctly because it is not necessary for the antenna to lay flat against the tissue. The waveguide radiation pattern may tend to be more directed as well.

While some variations of the present invention have been discussed, those skilled in the art will be able to appreciate that many other possibilities are available after reviewing the teachings of the present invention. As well, while the features of the present invention have been discussed as to heart tissues, it is anticipated that the teachings of the present invention could be applied to other applications such as heating tumors in prostrate glands or reducing the size of such glands. While significant improvement can be expected with continued use of the development tools discussed above, the transcather antenna of the present invention has already been tested in the test apparatus to produce temperature increases of 22° C. at beef heart tissue depths of 10.5 millimeters without surface charring and only a small increase of the saline test solution used to simulate the blood surrounding the catheter and antenna. For this particular test, the gap in the antenna was 1.0 centimeter, the frequency of operation was 3.95 Gigahertz, the heating time was 5 minutes, the power level was 14 watts, and the SWR was 1.27 at the catheter input and 1.39 at the antenna input.

The foregoing disclosure and description of the invention are illustrative and explanatory thereof, and various changes in the method steps and also the details of the apparatus may be made within the scope of the appended claims without departing from the spirit of the invention.

What is claimed is:

1. A method for thermally ablating arrhythmogenic cardiac tissue to treat arrhythmias while controlling temperature rise of proximately located blood and heart tissues, comprising:

providing a catheter with a microwave radiator at one end thereof;

selecting a frequency of operation for said microwave radiator within a frequency range of from 1.0 Gigahertz to 12.0 Gigahertz;

selecting a microwave power level of operation such that heat rise in said proximately located blood and a surface of said heart tissues due to absorption of microwave energy at said frequency of operation is limited by a blood flow rate and a specific heat of said blood to within a selected temperature rise;

determining a heating time for said arrhythmogenic cardiac tissue such that a combination of absorption of microwave energy at said frequency of operation and thermal conductivity of said arrhythmogenic cardiac tissue results in a sufficient temperature rise for thermal ablation of said arrhythmogenic cardiac tissue, said selected temperature rise of said of said proximally located blood and said surface of said heart tissues being less than said sufficient temperature rise for thermal ablation of said arrhythmogenic cardiac tissue;

positioning said catheter such that said microwave radiator is adjacent said arrhythmogenic cardiac tissue and is within said blood flow; and conducting a microwave signal through said catheter to said cardiac tissue.

2. The method of claim 1, further comprising: maintaining said frequency of operation of said microwave power in the range of from 2.0 Gigahertz to 6.0 Gigahertz.

3. The method of claim 1 further comprising:

determining said blood temperature rise along a surface of said microwave radiator.

4. The method of claim 1 further comprising:

providing said catheter with a co-axial cable structure.

5. The method of claim 1, wherein:

said selecting of a microwave power level of operation is made such that heat rise in said proximally located blood due to absorption of microwave energy at said frequency of operation is limited by a blood flow rate and a specific heat of said blood to within a selected temperature rise less than about 2° C.

6. The method of claim 1, further comprising:

providing said catheter with a non-helical microwave radiator at one end thereof.

7. The method of claim 1, further comprising:

providing said catheter with a monopole disk-loaded cylindrical wire microwave radiator at one end thereof.

8. A method for thermally ablating arrhythmogenic cardiac tissue to treat arrhythmias while controlling temperature rise of proximately located blood and heart tissues, comprising:

providing a catheter with a microwave radiator at one end thereof;

selecting a frequency of operation for said microwave radiator within a frequency range of from 1.0 Gigahertz to 12.0 Gigahertz;

selecting a microwave power level of operation such that heat rise in said proximally located blood due to absorption of microwave energy at said frequency of operation is limited by a blood flow rate and a specific heat of said blood to within a selected temperature rise;

determining a heating time for said arrhythmogenic cardiac tissue such that a combination of absorption of microwave energy at said frequency of operation and thermal conductivity of said arrhythmogenic cardiac tissue results in sufficient temperature rise for thermal ablation of said arrhythmogenic cardiac tissue;

positioning said catheter such that said microwave radiator is adjacent said arrhythmogenic cardiac tissue and is within said blood flow;

conducting a microwave signal through said catheter to said cardiac tissue; and attenuating surface microwaves along said catheter by about 20 decibels.

9. A method for thermally ablating arrhythmogenic cardiac tissue to treat arrhythmias while controlling temperature rise of proximately located blood and heart tissues, comprising:

providing a catheter with a microwave radiator at one end thereof;

selecting a frequency of operation for said microwave radiator within a frequency range of from 1.0 Gigahertz to 12.0 Gigahertz;

selecting a microwave power level of operation such that heat rise in said proximally located blood due to absorption of microwave energy at said frequency of operation is limited by a blood flow rate and a specific heat of said blood to within a selected temperature rise;

determining a heating time for said arrhythmogenic cardiac tissue such that a combination of absorption of microwave energy at said frequency of operation and thermal conductivity of said arrhythmogenic cardiac tissue results in sufficient temperature rise for thermal ablation of said arrhythmogenic cardiac tissue;

positioning said catheter such that said microwave radiator is adjacent said arrhythmogenic cardiac tissue and is within said blood flow;

conducting a microwave signal through said catheter to said cardiac tissue; and providing a catheter surface wave antennuator adjacent said microwave radiator end.

10. A method for thermally ablating arrhythmogenic cardiac tissue to treat arrhythmias while controlling temperature rise of proximately located blood and heart tissues, comprising:

providing a catheter with a microwave radiator at one end thereof; selecting a frequency of operation for said microwave radiator within a frequency range of from 1.0 Gigahertz to 12.0 Gigahertz, selecting said frequency of operation for controlling a desired lesion volume from frequencies within said frequency range of from 1.0 Gigahertz to 12.0 Gigahertz, said desired lesion volume being variable with respect to said frequency of operation within said frequency range of from 1.0 Gigahertz to 12.0 Gigahertz;

selecting a microwave power level of operation such that heat rise in said proximally located blood due to absorption of microwave energy at said frequency of operation is limited by a blood flow rate and a specific heat of said blood to within a selected temperature rise;

determining a heating time for said arrhythmogenic cardiac tissue such that a combination of absorption of microwave energy at said frequency of operation and thermal conductivity of said arrhythmogenic cardiac tissue results in sufficient temperature rise for thermal ablation of said arrhythmogenic cardiac tissue;

positioning said catheter such that said microwave radiator is adjacent said arrhythmogenic cardiac tissue and is within said blood flow; and conducting a microwave signal through said catheter to said cardiac tissue.

11. A method for thermally ablating arrhythmogenic cardiac tissue to treat arrhythmias while controlling temperature rise of proximately located blood and heart tissues, comprising:

providing a catheter with a microwave radiator at one end thereof;

selecting a frequency of operation for said microwave radiator within a frequency range of from 1.0 Gigahertz to 12.0 Gigahertz;

selecting a microwave power level of operation such that heat rise in said proximally located blood due to absorption of microwave energy at said frequency of operation is limited by a blood flow rate and a specific heat of said blood to within a selected temperature rise;

determining a heating time for said arrhythmogenic cardiac tissue such that a combination of absorption of microwave energy at said frequency of operation and thermal conductivity of said arrhythmogenic cardiac tissue results in sufficient temperature rise for thermal ablation of said arrhythmogenic cardiac tissue;

positioning said catheter such that said microwave radiator is adjacent said arrhythmogenic cardiac tissue and is within said blood flow;

conducting a microwave signal through said catheter to said cardiac tissue; and maintaining a standing wave ratio on said catheter of less than three to one at an antenna input.

12. The method of claim 11 wherein said step of maintaining a standing wave further comprises:

maintaining said standing wave ratio of less than three to one from approximately 1.5 Gigahertz to more than 8.0 Gigahertz for effecting a broad bandwidth.

13. The method of claim 11 wherein said step of maintaining a standing wave further comprises maintaining a standing wave ratio of less than two to one from approximately 1.5 Gigahertz to more than 8.0 Gigahertz for effecting good impedance matching over a broad bandwidth.

14. A method for thermally ablating arrhythmogenic cardiac tissue to treat arrhythmias while controlling temperature rise of proximately located blood and heart tissues, comprising:

providing a catheter with a microwave radiator at one end thereof providing said catheter with a waveguide structure such that said microwave waveguide has an outer conductor defining a waveguide cavity, said waveguide cavity being filled with an inner insulative material of selected permittivity, said waveguide cavity having no inner conductor therein such that said microwave waveguide is not a coaxial cable;

selecting a frequency of operation for said microwave radiator within a frequency range of from 1.0 Gigahertz to 12.0 Gigahertz;

selecting a microwave power level of operation such that heat rise in said proximally located blood due to absorption of microwave energy at said frequency of operation is limited by a blood flow rate and a specific heat of said blood to within a selected temperature rise;

determining a heating time for said arrhythmogenic cardiac tissue such that a combination of absorption of microwave energy at said frequency of operation and thermal conductivity of said arrhythmogenic cardiac tissue results in sufficient temperature rise for thermal ablation of said arrhythmogenic cardiac tissue;

positioning said catheter such that said microwave radiator is adjacent said arrhythmogenic cardiac tissue and is within said blood flow; and conducting a microwave signal through said catheter to said cardiac tissue.

15. A method for thermally ablating arrhythmogenic cardiac tissue to treat arrhythmias while controlling temperature rise of proximately located blood and heart tissues, comprising:

providing a catheter with at least three microwave radiators at one end thereof such that each of said at least three microwave radiators is formed from at least three physical discontinuities in a non-helical monopole antenna such that substantially all microwave radiation from said antenna is emitted from said at least three physical discontinuities;

selecting a frequency of operation for said microwave radiator within a frequency range of from 1.0 Gigahertz to 12.0 Gigahertz;

selecting a microwave power level of operation such that heat rise in said proximally located blood due to absorption of microwave energy at said frequency of operation is limited by a blood flow rate and a specific heat of said blood to within a selected temperature rise;

determining a heating time for said arrhythmogenic cardiac tissue such that a combination of absorption of microwave energy at said frequency of operation and thermal conductivity of said arrhythmogenic cardiac tissue results in sufficient temperature rise for thermal ablation of said arrhythmogenic cardiac tissue;

positioning said catheter such that said microwave radiator is adjacent said arrhythmogenic cardiac tissue and is within said blood flow; and conducting a microwave signal through said catheter to said cardiac tissue.

* * * * *